United States Patent
Cho et al.

(10) Patent No.: US 8,191,715 B2
(45) Date of Patent: Jun. 5, 2012

(54) CENTRIFUGAL FORCE-BASED MICROFLUIDIC DEVICE AND MICROFLUIDIC SYSTEM INCLUDING THE SAME

(75) Inventors: Yoon-kyoung Cho, Suwon-si (KR); Beom-seok Lee, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1105 days.

(21) Appl. No.: 12/056,345

(22) Filed: Mar. 27, 2008

(65) Prior Publication Data

US 2008/0237151 A1 Oct. 2, 2008

(30) Foreign Application Priority Data

Apr. 2, 2007 (KR) .................. 10-2007-0032500
Apr. 2, 2007 (KR) .................. 10-2007-0032501

(51) Int. Cl.
*B01D 17/038* (2006.01)
*B01L 3/00* (2006.01)
*G01N 21/07* (2006.01)

(52) U.S. Cl. ........ 210/380.1; 210/360.1; 494/2; 494/43; 436/45; 436/180; 422/72; 422/506; 422/533

(58) Field of Classification Search ............... 210/360.1, 210/380.1; 494/2, 43; 436/45, 180; 422/72, 422/506, 533
See application file for complete search history.

(56) References Cited

U.S. PATENT DOCUMENTS

| 5,061,381 A | 10/1991 | Burd |
| 5,242,606 A | 9/1993 | Braynin et al. |
| 5,588,946 A | 12/1996 | Graham et al. |
| 2004/0120856 A1 | 6/2004 | Andersson et al. |
| 2006/0240964 A1 | 10/2006 | Lolachi et al. |

FOREIGN PATENT DOCUMENTS

| DE | 2850992 A1 | 6/1980 |
| EP | 0688606 A1 | 6/1995 |
| EP | 1900433 A2 | 6/2007 |
| EP | 1935492 A1 | 10/2007 |
| EP | 1980322 A1 * | 10/2008 |
| WO | 0078455 A1 | 12/2000 |
| WO | 0243866 A2 | 6/2002 |

OTHER PUBLICATIONS

Communication issued on Nov. 17, 2010 in the corresponding European Patent Application No. 08153832.4.
Jong-Myeon Park et al: Multifunctional microvalves control by optical illumination on nanoheaters and its application in centrifugal microfluidic devices, vol. 7, Feb. 15, 2007 pp. 557-564, XP007902269.

* cited by examiner

*Primary Examiner* — David A Reifsnyder
(74) *Attorney, Agent, or Firm* — Sughrue Mion, PLLC

(57) ABSTRACT

A centrifugal force-based microfluidic device in which a sample including particles and a fluid is centrifugally separated such that the separated fluid is quantitatively distributed, and a microfluidic system including the centrifugal force-based microfluidic device are provided. The centrifugal force-based microfluidic device includes a microfluidic structure in which, within a rotatable disc-shaped platform, a sample, including particles and a fluid, is quickly centrifugally separated into the particles and the fluid using the rotation of the disc-shaped platform and the fluid having a certain volume of the separated fluid is discharged by rotation of the disc-shaped platform.

25 Claims, 14 Drawing Sheets

CENTRIFUGAL FORCE-BASED MICROFLUIDIC DEVICE AND MICROFLUIDIC SYSTEM INCLUDING THE SAME

CROSS-REFERENCE TO RELATED PATENT APPLICATIONS

This application claims the benefit of Korean Patent Application No. 10-2007-0032500, filed on Apr. 2, 2007 and 10-2007-0032501, filed on Apr. 2, 2007, in the Korean Intellectual Property Office, the disclosures of which are incorporated herein in its entirety by reference.

BACKGROUND OF THE INVENTION

1. Field of the Invention

The present invention relates to a centrifugal force-based microfluidic device, and more particularly, to a centrifugal force-based microfluidic device in which a fluid and particles are separated from a sample, including the fluid and the particles, within a disc-shaped platform using a centrifugal force such that the separated fluid is quantitatively distributed, and a microfluidic system including the centrifugal force-based microfluidic device.

2. Description of the Related Art

In general, a microfluidic structure of a microfluidic device includes a chamber in which a small amount of fluid is confined, a channel through which the fluid flows, a valve that regulates the flow of the fluid, and several functional units that perform predetermined functions using the fluid and which may also include a basic structure such that a chamber, a channel, and a valve are combined. The arrangement of the microfluidic structure is disposed on a chip-shaped substrate so that a test involving a biochemical reaction can be performed on a small chip, which is referred to as a bio chip. Further, a device is manufactured so that the processing and manipulation of several steps can be performed on one chip, which is referred to as a lab-on-a chip.

A driving pressure is needed to convey the fluid within the microfluidic device. A capillary pressure or a separate pump generates this driving pressure. These days, microfluidic devices, in which microfluidic structures are disposed on a compact disc-shaped platform and which drive a fluid using a centrifugal force, have been suggested, and are also referred to as a Lab CD or a Lab-on a disk. However, since these microfluidic devices are not fixed on a frame, but instead rotated, these devices are different from a Lab-on a chip, which operates while being fixed on the bottom of a frame in several aspects. It is easy to perform a centrifugal separation operation using a centrifugal force, but it is difficult to drive a separate valve or make a local temperature adjustment.

However, in the fields of biochemistry, biology, and medical science in which the microfluidic device is typically used, these microfluidic devices are required to have the function of separating particles from a sample, such as a biological sample of blood, saliva, and urine, in which a fluid and the particles are mixed. In order to meet such requirements, U.S. Pat. No. 5,061,381 has been proposed. However, the microfluidic device disclosed therein is stilled required to perform the function of separating the particles and the fluid in a small region within a disc-shaped platform. Furthermore, the microfluidic device is required to have the function of quantitatively distributing the fluid that is separated without going through a metering step involving the use of an additional unit.

SUMMARY OF THE INVENTION

The present invention provides a centrifugal force-based microfluidic device in which a fluid and particles are separated from a sample, including the fluid and the particles, within a disc-shaped platform by using a centrifugal force such that the separated fluid is quantitatively distributed, and a microfluidic system including the centrifugal force-based microfluidic device.

According to an exemplary aspect of the present invention, there is provided a centrifugal force-based microfluidic device comprising: a disc-shaped platform which can be rotated; a sample injection hole which is disposed at one side of the disc-shaped platform; a sample separation unit of which one end is connected to the sample injection hole, and which is extended toward the outside of the disc-shaped platform so as to provide a space in which a sample, including particles injected through the sample injection hole, is centrifugally separated into the particles and a fluid by rotation of the disc-shaped platform; and at least one outlet valve, which is connected to the sample separation unit, is separately driven, and is disposed in a position in which a fluid having a certain volume of the separated fluid within the sample separation unit can be discharged by rotation of the disc-shaped platform.

The device may further comprise a particle collecting unit, which is disposed at an outer end in a radial direction of the sample separation unit, is connected to the sample separation unit, and provides a space in which particles separated by centrifugal separation are collected. The particle collecting unit may be formed to have a depth that is greater than a depth of the sample separation unit, and a step portion that is formed at an interface between the particle collecting unit and the sample separation unit. The depth of the sample separation unit may be uniform or may gradually increase radially toward the outside of the disc-shaped platform.

The device may further comprise a sample storing unit, which is disposed at an inner end in a radial direction of the sample separation unit, is connected to the sample injection hole and accommodates the sample injected through the sample injection hole. The device may further comprise a surplus fluid collecting unit which is connected to an inner end in a radial direction of the sample separation unit and accommodates a surplus fluid that exceeds a predetermined capacity of the sample separation unit. The surplus fluid collecting unit may comprise a channel that is connected to the sample separation unit and a valve that controls a flow of the fluid through the channel passively or actively. The device may further comprise both the above-described particle collecting unit and the above-described surplus fluid collecting unit. Even in this case, the depth of the sample separation unit may be uniform or may gradually increase radially toward the outside of the disc-shaped platform.

The sample separation unit may be disposed to have an inclination with respect to a radial direction of the disc-shaped platform.

According to another aspect of the present invention, there is provided a centrifugal force-based microfluidic device comprising: a platform which can be rotated; a sample injection hole which is disposed at one side of the platform; a sample movement unit of which one end is connected to the sample injection hole and which is extended toward the outside of the platform; a particle collecting unit which is disposed at an outer end of the sample movement unit so as to provide a space in which particles having relatively high densities can be collected from the sample movement unit by rotation of the platform; a fluid collecting channel which is connected to the particle collecting unit and which has an inner end connected to a vent hole disposed to be nearer to a rotation center of the platform than the particle collecting unit so that a fluid of a sample is collected by rotation of the platform; and at least one outlet valve which is connected to the fluid collecting channel, which is separately driven and which is disposed in a position in which a fluid having a certain volume of the separated fluid within the fluid collecting channel can be discharged by rotation of the platform.

An outer end of the fluid collecting channel may be connected to the particle collecting unit and a depth of the fluid collecting channel may be less than that of the particle collecting unit so that a step portion is formed at an interface between the particle collecting unit and the fluid collecting channel. The particle collecting unit may be formed to have a depth that is greater than the sample movement unit so that a step portion is formed between the particle collecting unit and the sample movement unit. A depth of the fluid collecting channel may be less than that of the sample movement unit.

The depth of the sample separation unit may gradually increase radially toward the outside of the platform.

The device may further comprise a sample storing unit which is disposed at an inner end in a radial direction of the sample separation unit, is connected to the sample injection hole and accommodates the sample injected through the sample injection hole.

The sample movement unit may be disposed to have an inclination with respect to a radial direction of the disc-shaped platform. The sample movement unit may be divided into at least one barrier rib which is disposed in a longitudinal direction and provides a plurality of flow paths.

The centrifugal force-based microfluidic device may further comprise a normally open valve which is disposed between the particle collecting unit and the nearest outlet valve from the particle collecting unit and closes the fluid collecting channel.

According to another aspect of the present invention, there is provided a centrifugal force-based microfluidic system comprising: a centrifugal force-based microfluidic system comprising a platform which can be rotated, a sample injection hole which is disposed at one side of the platform, a sample movement unit of which one end is connected to the sample injection hole and which is extended toward an outside of the platform, a particle collecting unit which is disposed at an outer end of the sample movement unit so as to provide a space in which particles having relatively high densities can be collected from the sample movement unit by rotation of the platform, a fluid collecting channel which is connected to the particle collecting unit and which has an inner end connected to a vent hole disposed to be nearer to a rotation center of the platform than the particle collecting unit so that a fluid of a sample is collected by rotation of the platform, and at least one outlet valve which is connected to the fluid collecting channel, which is separately driven and which is disposed in a position in which a fluid having a predetermined volume of the separated fluid within the fluid collecting channel can be discharged by rotation of the platform; a rotation driver which supports the centrifugal force-based microfluidic device and controllably rotates the centrifugal force-based microfluidic device; and a valve driving unit which separately drives a valve selected in the centrifugal force-based microfluidic device.

The valve driving unit may comprise: an external energy source which emits an electromagnetic wave capable of inducing heating of the heat generating particles within the valve; and an external energy source adjusting unit which adjusts the position or direction of the external energy source so that an electromagnetic wave radiated by the external energy source can reach a region, corresponding to the selected valve. The external energy source adjusting unit may comprise a linear movement unit which moves the external energy source that is installed toward the platform of the centrifugal force-based microfluidic device in a radial direction of the disc-shaped platform, or a plane moving unit which moves the external energy source installed toward the disc-shaped platform in two directions on a plane parallel to the disc-shaped platform according to rectangular coordinates.

BRIEF DESCRIPTION OF THE DRAWINGS

Aspects of the present invention will become more apparent by describing in detail exemplary embodiments thereof with reference to the attached drawings in which.

DETAILED DESCRIPTION OF EXEMPLARY EMBODIMENTS

Figure 1:
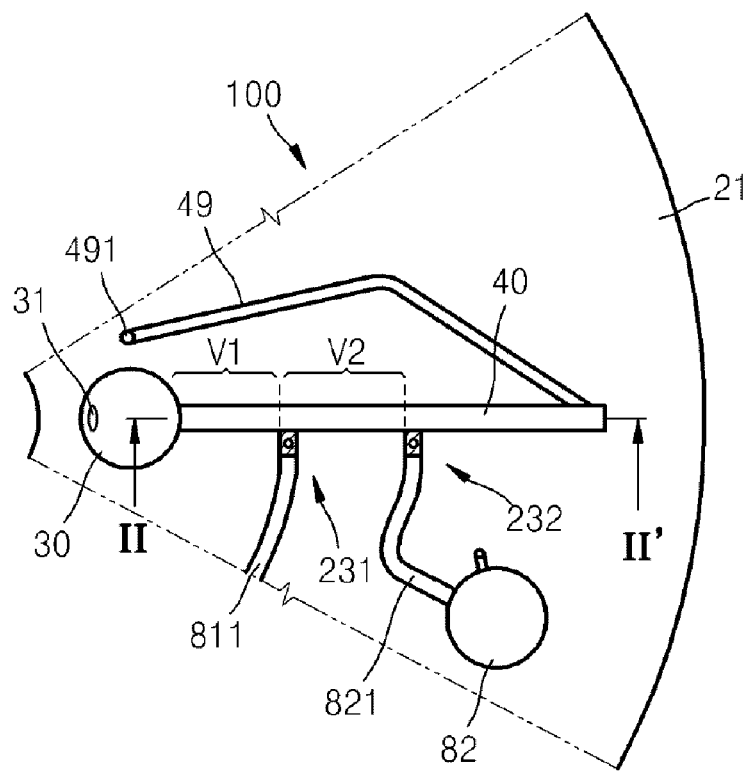
FIG. 1 is a plan view of a centrifugal force-based microfluidic device according to an exemplary embodiment of the present invention.

The present invention will now be described more fully with reference to the accompanying drawings, in which exemplary embodiments of the invention are shown. Like reference numerals in the drawings denote like elements, and thus their description will be omitted. The shape of a structure of a chamber and a channel may be simplified, and the ratio of their sizes may be expanded or reduced as compared to actuality. Here, a sample is a biological sample such as blood, saliva, and urine and refers to material in which a fluid and particles having higher densities than the fluid are mixed. In addition, an inside and an outside of a platform denote a side near to the rotation center of the platform and a side distant from the rotation center of the platform, respectively.

FIG. 1 is a plan view of a centrifugal force-based microfluidic device 100 according to an embodiment of the present invention. According to the present embodiment, the centrifugal force-based microfluidic device 100 includes a disc-shaped platform 21, a sample separation unit 40, a sample storage unit 30, a vent channel 49, a test unit 82, a first distribution channel 811, and a second distribution channel 821 which provide a space of the disc-shaped platform 21 in which a fluid is accommodated or a flow path through which the fluid flows.

The disc-shaped platform 21 is formed of a plastic material of which is easily formed and which has a surface which is biologically non-activated. However, the material of the disc-shaped platform 21 is not limited to this and can be a material having chemical and biological stability, optical transparency, and mechanical workability. The disc-shaped platform 21 can be constructed with two or more disc-shaped plates. An engraved structure corresponding to a chamber or a channel is formed on a surface of one plate facing the other plate, and the places are bonded to provide a space and a path inside the disc-shaped platform 21. The plates of the disc-shaped platform may be bonded using various methods such as adhesion using an adhesive, a double-sided adhesive tape, ultrasonic wave fusion, or laser welding.

The centrifugal force-based microfluidic device 100 includes the sample separation unit 40 that centrifugally separates a fluid from a sample containing particles by rotation of the disc-shaped platform 21. The sample separation unit 40 is formed as a channel; however the present invention is not limited thereto. The sample separation unit 40 may be disposed so that its longitudinal direction, which is relatively greater than its latitudinal direction, is from an inside (side near the center) of the disc-shaped platform 21 to an outside (side distant from the center) of the disc-shaped platform 21. The size of the sample separation unit 40 is also not limited to that of the present invention, and may be determined according to the radius and thickness of the disc-shaped platform 21 and the amount of a sample that is to be centrifugally separated and distributed, and the size of the particles mixed in the sample.

A sample injection hole 31, through which the sample is injected from the outside, is formed at an inner end of the sample separation unit 40. However, the centrifugal force-based microfluidic device 100 may further include the sample storage unit 30 which is connected to the sample injection hole 31 and the sample separation unit 40, and primarily accommodates the sample injected through the sample injection hole 31, so as to supply the sample to the sample separation unit 31 during rotation of the disc-shaped platform 21. The sample storage unit 30 can have the shape of a chamber, as illustrated in FIG. 1. The vent channel 49 is connected to an outer end of the sample separation unit 40. A vent hole 491 of the vent channel 49 is disposed nearer to the center of the disc-shaped platform 21 than the inner end of the sample separation unit 40, so as to prevent the fluid from leaking during centrifugal separation of a sample using a centrifugal force.

At least one outlet valve from among a first outlet valve 231 and a second outlet valve 232 that are included in the centrifugal force-based microfluidic device 100 is disposed at a middle portion of the sample separation unit 40 (a portion between the inner and outer ends of the sample separation unit 40). When there are more than the two first and second outlet valves 231 and 232, the first and second outlet valves 231 and 232 are separately driven such that the one placed near to the center of the disc-shaped platform 21 is driven first. When the two outlet valves are the first outlet valve 231 and the second outlet valve 232, as shown in FIG. 1, respectively, if the centrifugal force-based microfluidic device 100 opens the first outlet valve 231 and rotates the disc-shaped platform 21, a fluid V1, which is filled in an inner side than the first outlet valve 231 within the sample separation unit 40, is exhausted through the first distribution channel 811, and if the centrifugal force-based microfluidic device 100 opens the second outlet valve 232 and rotates the disc-shaped platform 21, a fluid V2, which is placed between the first outlet valve 231 and the second outlet valve 232 within the sample separation unit 40, is exhausted through a second distribution channel 821 and is conveyed to the test unit 82. Through the above structure, the centrifugal force-based microfluidic device 100 according to the present invention can centrifugally separate the fluid from the sample containing the particles and the fluid and distribute the separated fluid by dividing the fluid into a certain volume.

In the present embodiment, the test unit 82, which accommodates the quantitatively-distributed fluid, is disposed in various ways according to the usage of the centrifugal force-based microfluidic device 100, and the test unit 82 is simply in the form of a channel, as shown in FIG. 1. However, the test unit 82 is not limited there to, and can be a unit, which uses the fluid separated from the sample and is quantitatively distributed, and which is disposed inside the disc-shaped platform 21.

Figure 2A:
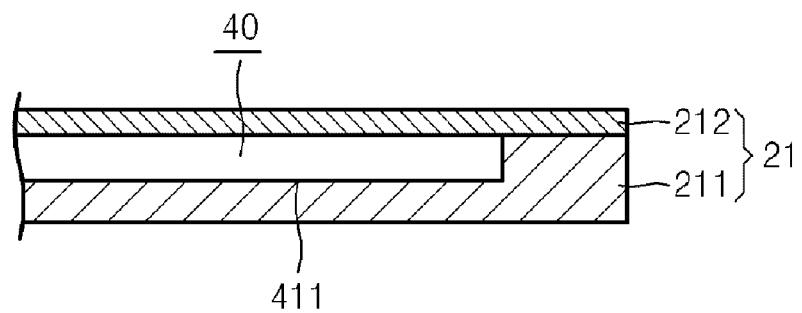
FIG. 2A is a cross-sectional view of a sample separation unit shown in FIG. 1 taken along line II-II'.

FIG. 2A is a cross-sectional view of the sample separation unit 40 taken along line II-II' of FIG. 1. The disc-shaped platform 21 includes an upper plate 212 and a lower plate 211, and the upper surface of the lower plate 211 is engraved to provide the sample separation unit 40. In this case, the depth of the engraving of the sample separation unit 40 is uniform from the inside of the disc-shaped platform 21 to the outside of the disc-shaped platform 21. That is, a bottom 411 of the sample separation unit 40 is continuously flat throughout the disc-shaped platform 21.

Figure 2B:
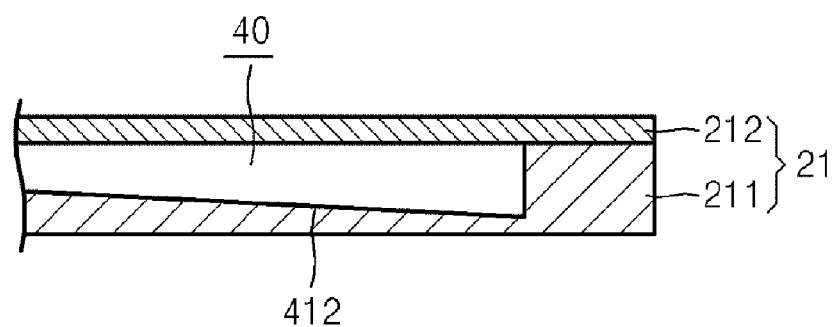
FIG. 2B is a cross-sectional view illustrating a modified example of a bottom of the sample separation unit illustrated in FIG. 2A.

FIG. 2B is a cross-sectional view illustrating a modified example of the bottom 411 of the sample separation unit 40 illustrated in FIG. 2A. According to the modified example of FIG. 2B, the sample separation unit 40 becomes deeper as it is placed nearer to the outside of the disc-shaped platform 21. That is, a bottom 412 of the sample separation unit 40 may be gradually radially declined toward the outside of the disc-shaped platform 21. When the sample is centrifugally separated, relatively heavy particles generally move to the outside of the disc-shaped platform 21 along the bottom 412 of the sample separation unit 40 due to the effect of gravity together with a centrifugal force. In this case, the interference between the outwardly-collecting particles and the inwardly-moving fluid is reduced due to the inclined bottom 412 so that centrifugal separation can be preformed within a shorter time.

Figure 3:
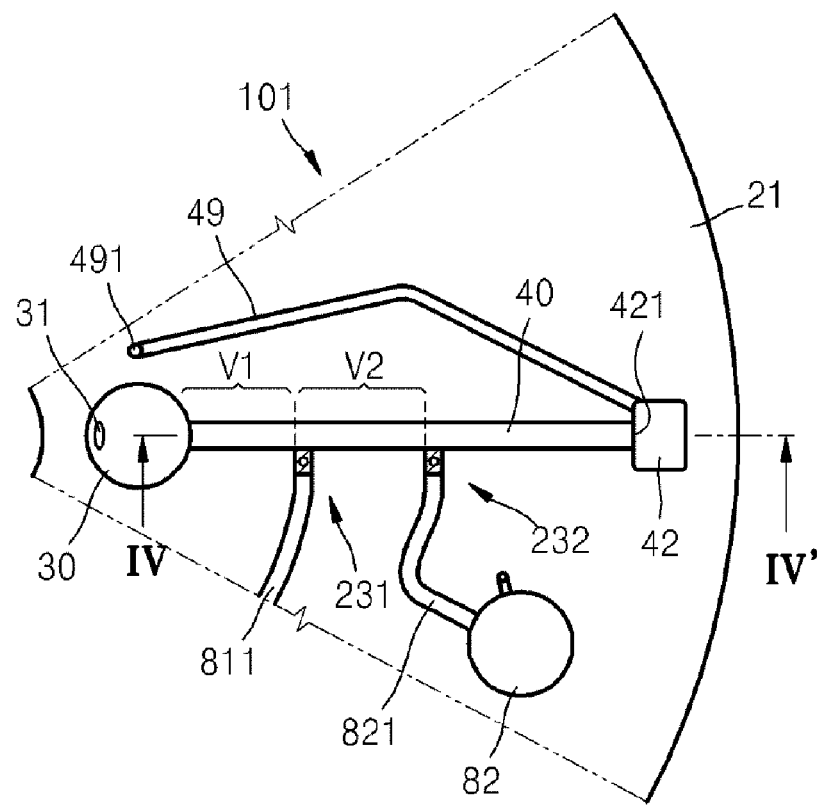
FIG. 3 is a plan view of a centrifugal force-based microfluidic device according to another exemplary embodiment of the present invention.

FIG. 3 is a plan view of a centrifugal force-based microfluidic device 101 according to another embodiment of the present invention. The centrifugal force-based microfluidic device 101 further includes a particle collecting unit 42 that is disposed at an outer end of the sample separation unit 40 to accommodate particles separated by centrifugal separation, as compared to the centrifugal force-based micro fluidic device 100 of FIG. 1. In this case, a step portion 421 that is formed at an interface between the sample separation unit 40 and the particle collecting unit 42, so that the depth of the sample separation unit 40 is not uniform. The frequency of the particles that are first separated by the step portion 421 flow backward in the sample separation unit 40 during fluid distribution can be reduced.

Figure 4A:
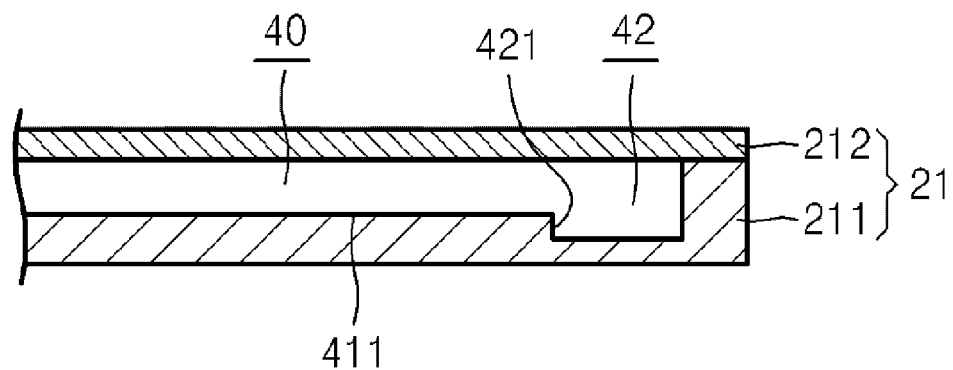
FIG. 4A is a cross-sectional view of a sample separation unit shown in FIG. 3 taken along line IV-IV'.
Figure 4B:
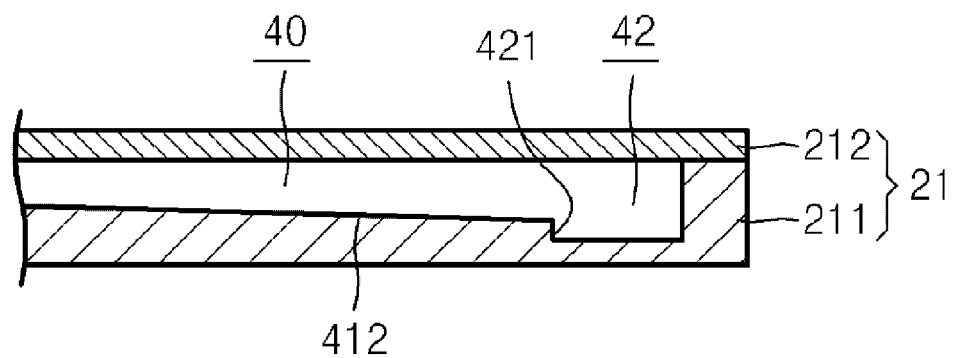
FIG. 4B is a cross-sectional view illustrating a modified example of a bottom of the sample separation unit shown in FIG. 4A.

FIG. 4A is a cross-sectional view of the sample separation unit 40 taken along line IV-IV' of FIG. 3, and FIG. 4B is a cross-sectional view illustrating a modified example of a bottom 411 of the sample separation unit 40 of FIG. 4A. Even in case that the centrifugal force-based microfluidic device 101 further includes the particle collecting unit 42, the depth of the sample separation unit 40 can be uniform, as in FIG. 4A, or can also be deepened radially toward an outside of the disc-shaped platform 21, as in FIG. 4B.

Figure 5:
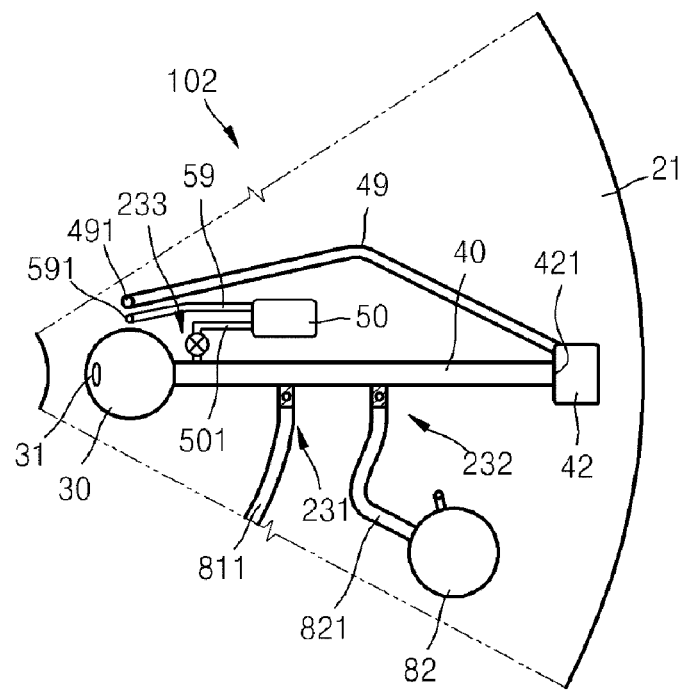
FIG. 5 is a plan view of a centrifugal force-based microfluidic device according to another exemplary embodiment of the present invention.

FIG. 5 is a plan view of a centrifugal force-based microfluidic device 102 according to another exemplary embodiment of the present invention. According to the present embodiment, the centrifugal force-based microfluidic device 102 may further include a surplus fluid collecting unit 50 as compared to the centrifugal force-based microfluidic device 101 of FIG. 3. The surplus fluid collecting unit 50 is connected to an inner end in a radial direction of the sample separation unit 40 through a channel 501, and a normally open valve 233 which controls the flow of the fluid. The normally open valve 233 is a passive valve that is passively opened when a predetermined pressure is applied to the valve, such as a capillary valve or a hydrophobic valve, or is a valve that is actively opened when power or energy is applied to the valve from the outside in response to an operating signal.

If the normally open valve 233 is a passive valve, for example, the surplus fluid collecting unit 50 is utilized. That is, if a sample that exceeds a predetermined capacity of the sample separation unit 40 is injected through the sample injection hole 31 during a centrifugal separation operation, the normally open valve 233 is opened by the pressure of a surplus fluid that acts on a portion to which the channel 501 is connected to the normally open valve 233, and the surplus fluid is collected in the surplus fluid collecting unit 50. As is obvious to one skilled in the art, the surplus fluid collecting portion 50 also has a vent channel 59 and a vent hole 591 connected to the vent channel 59. The centrifugal force-based microfluidic device 102, including the surplus fluid collecting unit 50, distributes a fixed quantity of fluid even when some errors occur when the sample is initially injected, manually.

In the present exemplary embodiment, the surplus fluid collecting unit 50 can be added to the centrifugal force-based microfluidic device 101 illustrated in FIGS. 3 through 5. However, as is obvious to one skilled in the art, the surplus fluid collecting unit 50 can also be added to the centrifugal force-based microfluidic device 100 illustrated in FIGS. 1 through 3 or a centrifugal force-based microfluidic device 103 of FIG. 6A which will be described below.

Figure 6A:
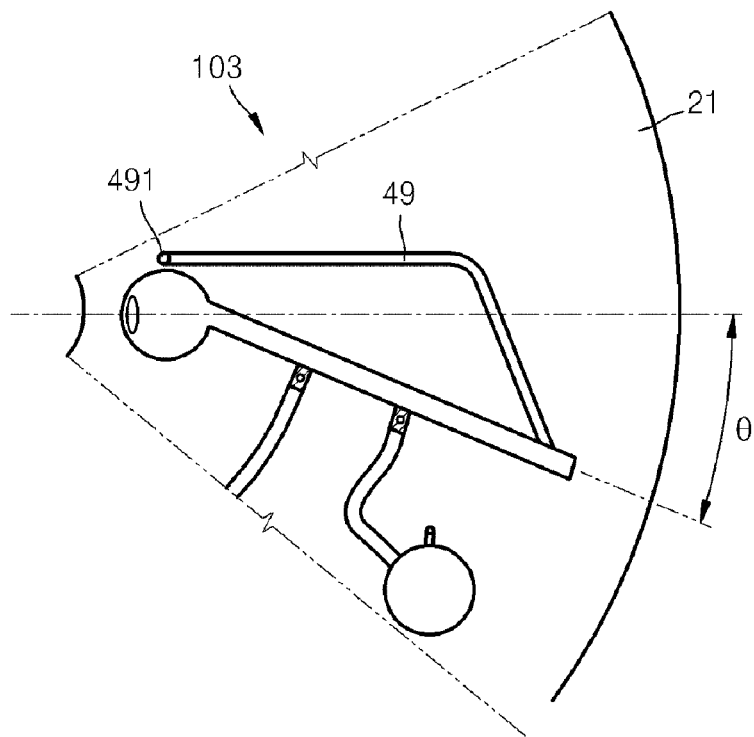
FIG. 6A is a plan view of a centrifugal force-based microfluidic device according to another exemplary embodiment of the present invention.

FIG. 6A is a plan view of the centrifugal force-based microfluidic device 103 according to another exemplary embodiment of the present invention. According to the present embodiment, the centrifugal force-based microfluidic device 103 includes the sample separation unit 44 of which an axis connecting inside and outside has a predetermined inclination θ with respect to a radial direction of the disc-shaped platform 21. In the present embodiment, the other portions, excluding the arrangement of the sample separation unit 44, are the same as those formed by combining the characterizing parts of any of the embodiments of the centrifugal force-based microfluidic devices 100, 101, 102 illustrated in FIGS. 1 through 5.

As illustrated in FIG. 6A, the sample separation unit 44 that has an inclination θ with respect to the radial direction of the disc-shaped platform 21, separates a path through which particles having relatively high densities move to the outside, when the sample is centrifugally separated within the centrifugal force-based microfluidic device 103, and a path through which a fluid having relatively low density moves to the inside to reduce interference between the particles and the fluid, thereby improving a centrifugal separation speed. The basic principle for improving the centrifugal separation speed by separating moving paths of materials having different densities during centrifugal separation is referred to as the so-called "Boycott effect", as disclosed in U.S. Pat. No. 5,588,946. The centrifugal force-based microfluidic device 103 improves the centrifugal separation speed using the above principle even within the disc-shaped platform 21 (not a test tube). Here, the inclination θ of the sample separation unit 44 is determined according to the size of the particles included in a sample that is to be centrifugally separated and the viscosity of the fluid.

Figure 6B:
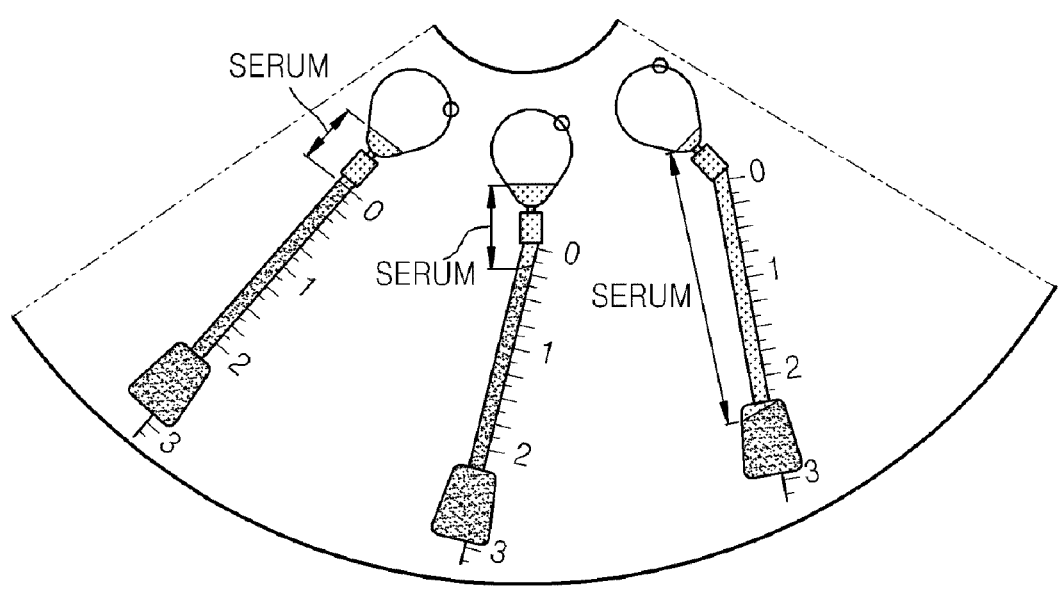
FIG. 6B is a plan view showing the centrifugal separation speed for when the angle of a sample separation unit of FIG. 6A with respect to a radial axis of a disc-shaped platform varied, according to an exemplary embodiment of the present invention.

FIG. 6B is a plan view showing the centrifugal separation speed for when the angle of the sample separation unit 40 of FIG. 6A in a radial axis of a disc-shaped platform 21 is varied, according to an embodiment of the present invention. In FIG. 6B, the left one of the three sample separation units shows that its longitudinal central axis is identical with the radial direction of a disc-shaped platform, and the middle one of the three sample separation units shows that the middle one has an inclination of 15 degrees with respect to the radial direction of the disc-shaped platform, and the right one of the three sample separation units shows that the right one has an inclination of 30 degrees with respect to the radial direction of the disc-shaped platform. The present experiment is used to check the centrifugal separation speed according to the inclination of the sample separation units, and thus, outlet valves connected to the sample separation units are not additionally provided in the centrifugal force-based micro fluidic device.

FIG. 6B shows the results in which a sample of 70 μl in which blood and a PBS buffer are mixed at a ratio of 1:1, is injected through the sample injection hole 31 and is centrifugally separated for about 80 seconds. In order to aid the checking, a scale in units of cm is marked in each sample separation unit. Referring to FIG. 6B, serum is separated only within about a scale mark of 0 cm in the left sample separation unit having an inclination of 0 degrees. Contrary to this, it can be ascertained through FIG. 6B that, in the middle sample separation unit that has an inclination of 15 degrees, serum is separated up to about 0.2 cm, and the right sample separation unit that has an inclination of 30 degrees, serum is separated up to about 2.25 cm. Thus, the inclination of the sample separation unit contributes to the improvement in centrifugal separation speed.

Figure 7:
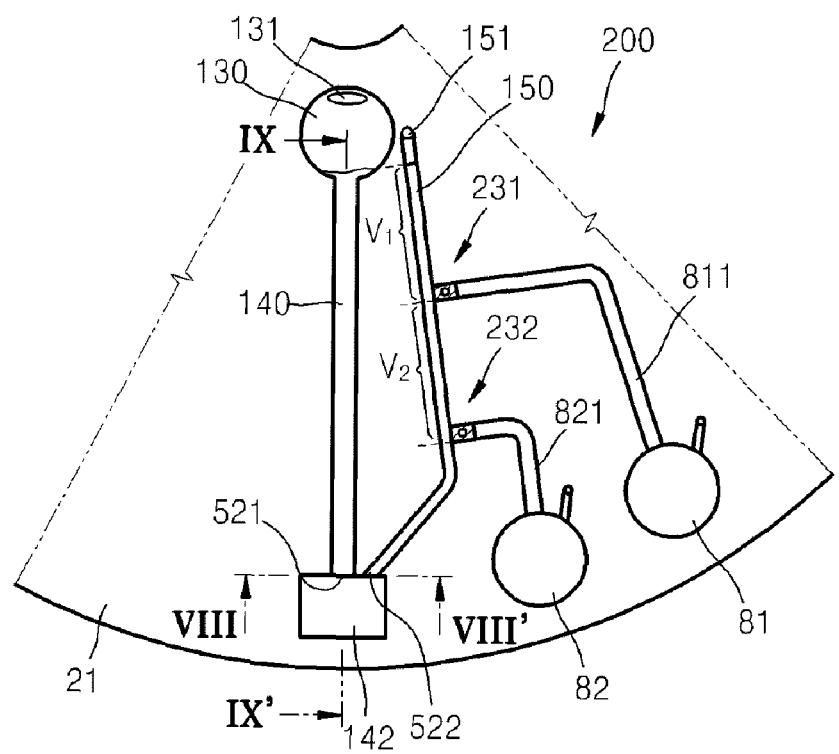
FIG. 7 is a plan view of a centrifugal force-based microfluidic device according to another exemplary embodiment of the present invention.

FIG. 7 is a plan view of a centrifugal force-based microfluidic device 200 according to another embodiment of the present invention. According to the present embodiment, the centrifugal force-based microfluidic device 200 includes the disc-shaped platform 21, a sample storage unit 130, a sample separation unit 140, a particle collecting unit 142, a fluid collecting channel 150, a first test unit 81, a second test unit 82, a first distribution channel 811, and a second distribution channel 821, which provide a space of the disc-shaped platform 21 in which a fluid is accommodated or a flow path through which the fluid flows.

The centrifugal force-based microfluidic device 200 includes the sample movement unit 140 which centrifugally separates a sample containing particles and a fluid by rotation of the disc-shaped platform 21. The sample movement unit 140 is formed in the form of a channel; however its shape is not limited thereto. The sample separation unit 140 may be disposed so that its longitudinal direction, which is relatively greater than its latitudinal direction, is from an inside (side near the center) of the disc-shaped platform 21 to an outside (side distant from the center) of the disc-shaped platform 21. The size of the sample separation unit 140 is also not limited, and is determined according to the radius and thickness of the disc-shaped platform 21, the amount of a sample that is to be centrifugally separated and distributed, and the size of the mixed particles in the sample.

A sample injection hole 131, through which the sample is injected from the outside, is formed at an inner end of an inside of the sample separation unit 140. However, the centrifugal force-based microfluidic device 200 can further include the sample storage unit 130 that is formed at the inner end of the sample separation unit 140. The sample storage unit 130 is connected to the sample injection hole 31 and the sample movement unit 140, primarily accommodates the sample that is injected through the sample injection hole 131 and supplies the sample to the sample movement unit 131 during rotation of the disc-shaped platform 21. Also, the sample storage unit 130 has the shape of a chamber, as illustrated in FIG. 7.

The particle collecting unit 142 is disposed at an outer end of the sample separation unit 140 to accommodate and confine outwardly-collecting particles of the sample, which are affected by the relatively large effects of a centrifugal force. The particle collecting unit 142 also provides a space in which at least one of its width and depth is greater than those of the sample movement unit 140, so as to sufficiently accommodate particles contained in the sample. The width and depth of the particle collecting unit 142 of FIG. 7 are greater than those of the sample movement unit 140. However, the present invention is not limited to this.

The fluid collecting channel 150 is connected to a portion of the particle collecting unit 142 to extend toward an inside of the disc-shaped platform 21 so that the fluid separated from the sample can be filled up to approximately the same level as the level of the sample within the sample movement unit 140. A vent hole 151 is formed at an inner end of the fluid collecting channel 150. The fluid collecting channel 150 also serves as a vent channel through which the sample enters the sample movement unit 140 and the particle collecting unit 142 from the sample injection hole 131. The vent hole 151 is disposed at an inner side (nearer to the center of the disc-shaped platform 21) than the inner end of the sample movement unit 140, so as to prevent the fluid from leaking.

The depth of the fluid collecting channel 150 may be shallower than that of the particle collecting unit 142. As such, part of the sample is filled up to some level in the fluid collecting channel 150, and particles do not enter the particle collecting unit 142. Particles of the sample having high density are affected by a centrifugal force due to rotation and gravity and are collected and confined on the outside and the bottom of the particle collecting unit 142. Thus, a fluid that is separated from the sample is filled into the fluid collecting channel 150. The width and depth of the fluid collecting channel 150 is determined according to the amount of a fluid that is to be separated and used, and in particular, the depth of the fluid collecting channel 150 is determined to be within the range in which the particles do not enter the fluid collecting channel 150 from the particle collecting unit 142 according to the capacity of the sample movement unit 140 and the particle collecting unit 142, the depth of the particle collecting unit 142, and the volume fraction of the particles of the sample that is mainly used.

Due to the Boycott effect (see U.S. Pat. No. 5,588,946), the time required for centrifugal separation is increased due to disturbance between the particles that radially move to the outside during centrifugal separation of the sample including the particles and the fluid that radially moves to the inside, and the movement path of the fluid and the particles is separated so that a centrifugal separation time can be reduced. However, according to the present invention, when the fluid is filled into the fluid collecting channel 150, the fluid is not disturbed by the movement of the particles. Thus, the fluid collecting channel 150 is filled only with the fluid that is separated from the sample even before centrifugal separation is performed.

At least one outlet valve is disposed at a middle portion of the fluid collecting channel 150 (between the vent hole 151 and an outer end of the fluid collecting channel 150 connected to the particle collecting unit 142). The centrifugal force-based microfluidic device 200 includes two outlet valves 231 and 232. When there are more than the two first and second outlet valves 231 and 232, the first and second outlet valves 231 and 232 are separately driven such that the one placed near the center of the disc-shaped platform 21 is driven first. When the two outlet valves are the first outlet valve 231 and the second outlet valve 232, respectively, if the centrifugal force-based microfluidic device 200 opens the first outlet valve 231 and rotates the disc-shaped platform 21, a fluid $V_1$ that is filled in on an inner side of the first outlet valve 231 is exhausted to the first test unit 81 through the first distribution channel 811, and if the centrifugal force-based microfluidic device 200 opens the second outlet valve 232 and rotates the disc-shaped platform 21, a fluid $V_2$ that is filled in on an inner side of the second outlet valve 232 is exhausted through the second distribution channel 821 and is conveyed to the second test unit 82. Through the above structure, the centrifugal force-based microfluidic device 200 according to the present invention can rapidly separate a required amount of fluid from the sample containing the particles and distribute the separated fluid by dividing the fluid into a predetermined volume.

In the present embodiment, the second test unit 82 which accommodates the quantitatively-distributed fluid is disposed in various ways according to the usage of the centrifugal force-based microfluidic device 200. The first and second test units 81 and 82 are simply in the form of a channel, as shown in FIG. 7. However, the first and second test units 82 are not limited thereto, and the first and second test units 82 each can be a unit which uses the fluid that is separated from the sample and quantitatively distributed, and be disposed inside the disc-shaped platform 21.

Figure 8:
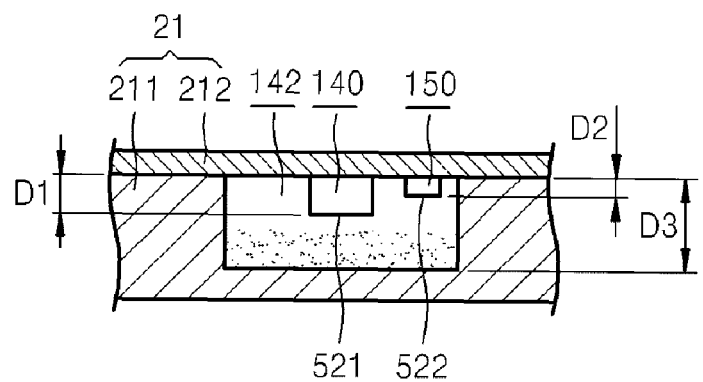
FIG. 8 is a cross-sectional view of the centrifugal force-based microfluidic device shown in FIG. 7 taken along line VIII-VIII'.

FIG. 8 is a cross-sectional view of the centrifugal force-based microfluidic device 200 taken along line VIII-VIII' of FIG. 7. The depth D2 of the fluid collecting channel 150 is shallower than the depth D3 of the particle collecting unit 142 (D3>D2), and a step portion 522 may be formed at an interface between the fluid collecting channel 150 and the particle collecting unit 142. Similarly, the depth D1 of the sample movement unit 140 is also shallower than the depth D3 of the particle collecting unit 142 (D3>D1), and a step portion 521 may be formed at an interface between the sample movement unit 140 and the particle collecting unit 142. Particles that are first separated by the step portions 521 and 522 can be prevented from entering the fluid collecting channel 150 and can reduce the frequency of the particles that are first separated by the step portions 521 and 522 flowing backward in the sample movement unit 140 during fluid distribution. Thus, the depth D2 of the fluid collecting channel 150 is shallower than the depth D1 of the sample movement unit 140.

Figure 9A:
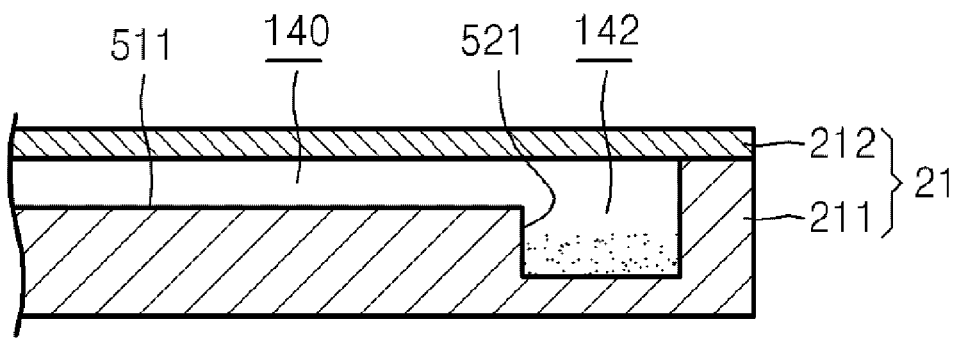
FIG. 9A is a cross-sectional view of the centrifugal force-based microfluidic device shown in FIG. 7 taken along line IX-IX'.

FIG. 9A is a cross-sectional view of the centrifugal force-based microfluidic device 200 taken along line IX-IX' of FIG. 7. The disc-shaped platform 21 includes the upper plate 212 and the lower plate 211, and the upper surface of the lower plate 211 is engraved to provide a space of the sample movement unit 140. In this case, the depth of the sample movement unit 140 is uniform from the inside of the disc-shaped platform 21 to the outside of the disc-shaped platform 21. That is, a bottom 511 of the sample movement unit 140 is continuously flat throughout the sample movement unit 140.

Figure 9B:
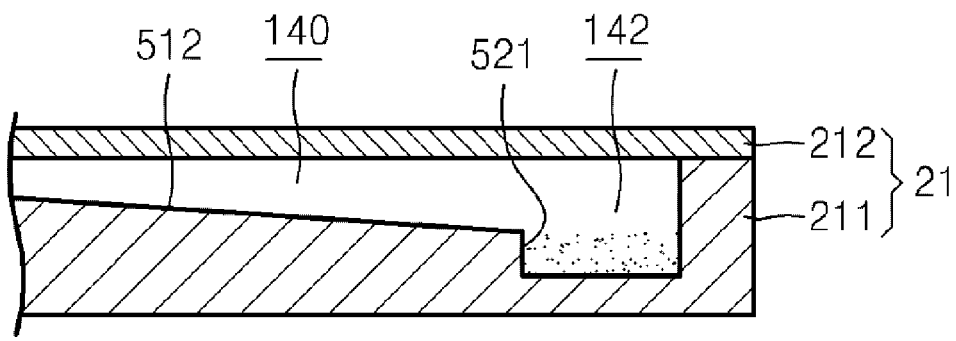
FIG. 9B is a cross-sectional view illustrating a modified example of a bottom of a sample movement unit illustrated in FIG. 9A.

FIG. 9B is a cross-sectional view illustrating a modified example of the bottom 511 of the sample movement unit 140 illustrated in FIG. 9A. According to the modified example of FIG. 9B, the sample movement unit 140 becomes deeper nearer to the outside of the disc-shaped platform 21. That is, a bottom 512 of the sample movement unit 140 may be gradually declined radially toward the outside of the disc-shaped platform 21. When the sample is centrifugally separated, relatively heavy particles generally move to the outside of the disc-shaped platform 21 along the bottom 512 of the sample movement unit 140 due to the effect of gravity together with centrifugal force. In this case, as illustrated in FIG. 9B, interference between the outwardly-collecting particles and the inwardly-moving fluid is reduced due to the inclined bottom 512 so that the movement of the sample and the centrifugal separation can be performed within a shorter time than the conventional case.

Figure 10:
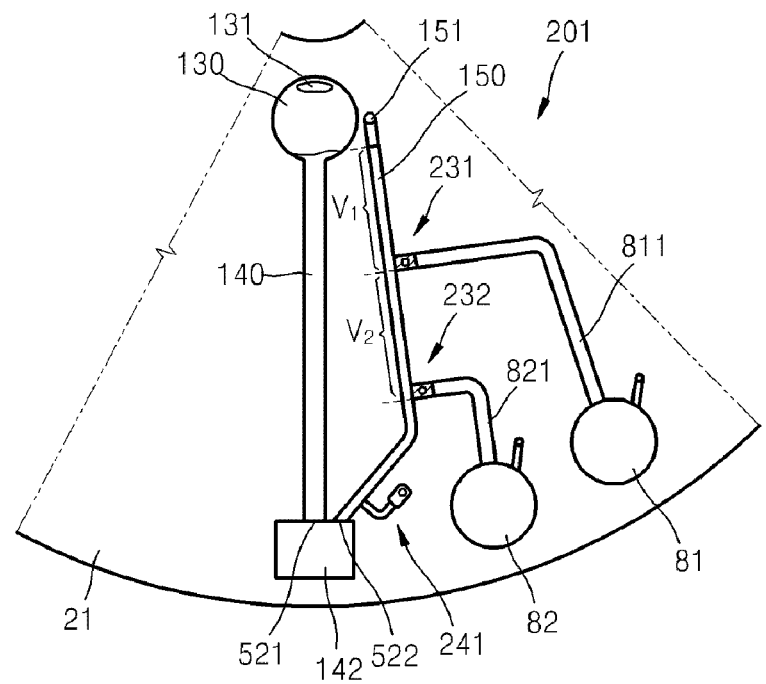
FIG. 10 is a plan view illustrating a centrifugal force-based microfluidic device according to another exemplary embodiment of the present invention.

FIG. 10 is a plan view illustrating a centrifugal force-based microfluidic device 201 according to another embodiment of the present invention. Compared to the centrifugal force-based microfluidic device 200 illustrated in FIG. 7, the centrifugal force-based microfluidic device 201 according to the present embodiment may further include a normally open valve 241 which operates after a fluid is separated from a sample and prevents the fluid from additionally entering the fluid collecting channel 150 from the particle collecting unit 142. The normally open valve 241 is disposed between the outside of the fluid collecting channel 150, more specifically, the outer end of the fluid collecting channel 150 connected to the particle collecting unit 142 and the nearest outlet valve from the particle collecting unit 142, in the present embodiment, the second outlet valve 232. There is no particular limitation in the operation and type of the normally open valve 241, that is, any valve that can perform the above-described function can be used and installed as the normally open valve 241.

Figure 11:
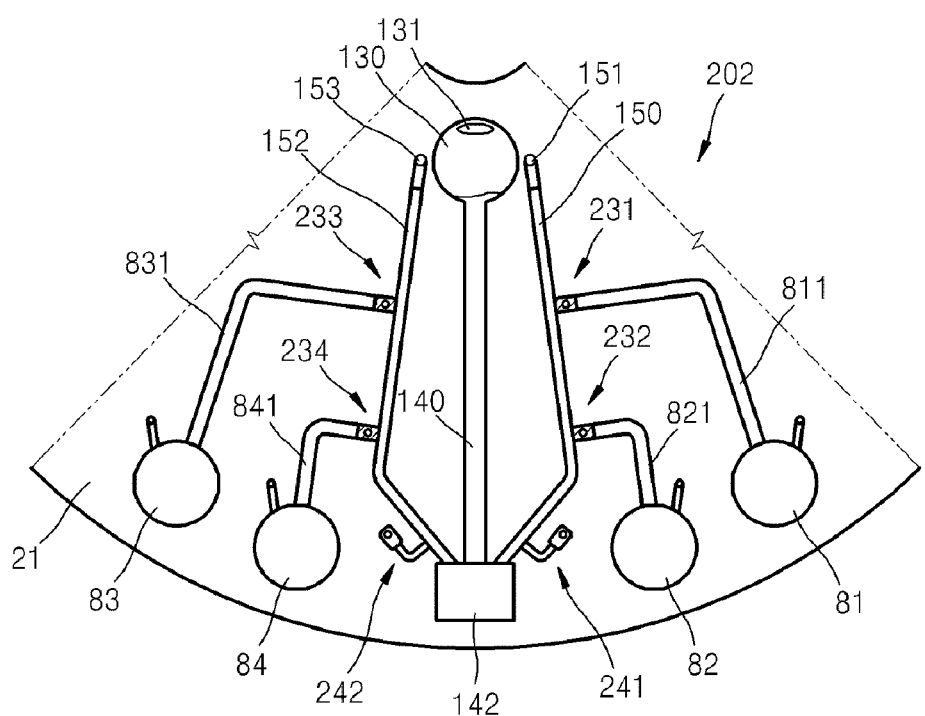
FIG. 11 is a plan view of a centrifugal force-based microfluidic device according to another exemplary embodiment of the present invention.

FIG. 11 is a plan view of a centrifugal force-based microfluidic device 202 according to another exemplary embodiment of the present invention. Compared to the centrifugal force-based microfluidic device 201 illustrated in FIG. 10, the centrifugal force-based microfluidic device 202 according to the present embodiment includes a first fluid collecting channel 150 and a second collecting channel 152 that correspond to the sample movement unit 140 and the particle collecting unit 142, respectively. If there is a sufficient space in the disc-shaped platform 21, more than two fluid collecting channels may also be disposed in the disc-shaped platform 21. The additional fluid collecting channel, as compared to the centrifugal force-based microfluidic device 201 of FIG. 10, is referred to as the second fluid collecting channel 152, and the second fluid collecting channel 152 has a vent hole 153 at the end inside of the disc-shaped platform 21 and third and fourth outlet valves 233 and 234 and a second normally open valve 242 are disposed on the second fluid collecting channel 152. That is, the third and fourth outlet valves 233 and 234 are respectively connected to third and fourth test units 83 and 84 through third and fourth distribution channels 831 and 841.

Figure 12:
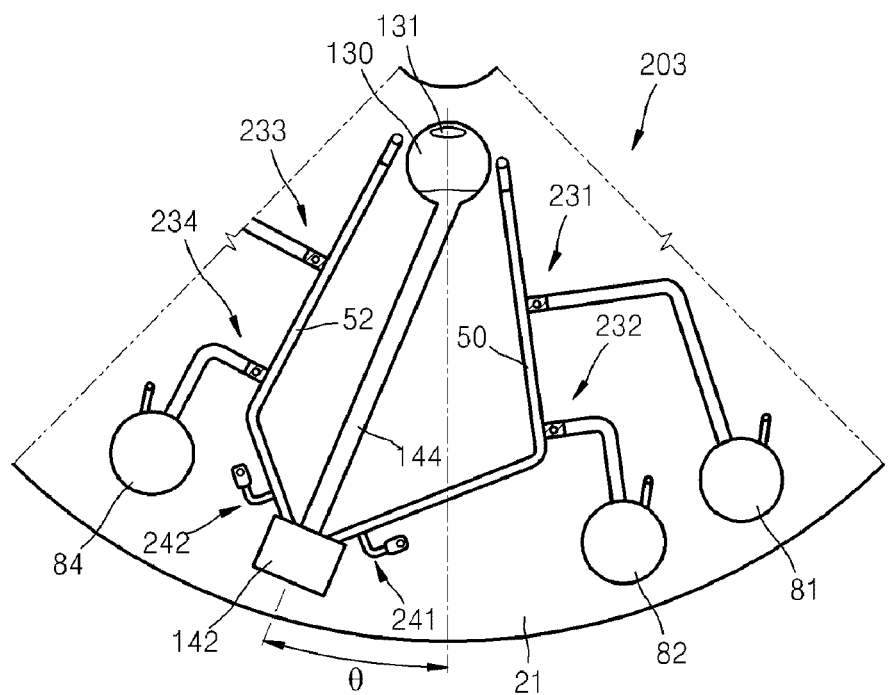
FIG. 12 is a plan view of a centrifugal force-based microfluidic device according to another exemplary embodiment of the present invention.

FIG. 12 is a plan view of a centrifugal force-based microfluidic device 203 according to another embodiment of the present invention. Compared to the centrifugal force-based microfluidic device 202 illustrated in FIG. 11, in the centrifugal force-based microfluidic device 203 according to the present embodiment, the sample movement unit 144 is inclined at a predetermined inclination angle θ with respect to a radial direction of the disc-shaped platform 21. In the above-descried structure in which the sample movement unit 144 is inclined, when a sample is centrifugally separated within the centrifugal force-based microfluidic device 203, a path in which particles that have a relatively high density move to the outside and a path in which a fluid that has a relatively low density moves to the inside are separate from each other to reduce interference between the particles and the fluid so that a centrifugal separation speed can be improved. The particles move to the particle collecting unit 142 mainly along the right wall surface of the sample movement unit 144. The inclination angle θ of the sample movement unit 144 is determined according to the size of the particles included in the sample that is to be centrifugally separated and the viscosity of the fluid.

Figure 13:
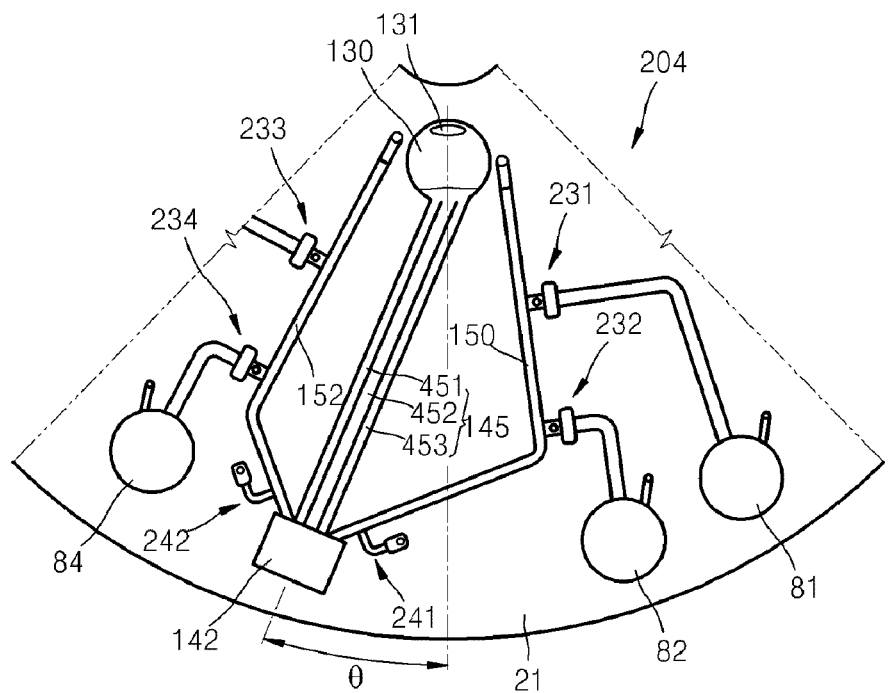
FIG. 13 is a plan view of a centrifugal force-based microfluidic device according to another exemplary embodiment of the present invention.

FIG. 13 is a plan view of a centrifugal force-based microfluidic device 204 according to another embodiment of the present invention. Compared to the centrifugal force-based microfluidic device 203 illustrated in FIG. 12, the centrifugal force-based microfluidic device 204 according to the present embodiment includes at least one barrier rib within a sample movement unit 145 so that the sample movement unit 145 is divided into a plurality of subchannels 451, 452, and 453. Like in the embodiment of FIG. 12, particles move to the particle collecting unit 142 along the right wall surface of each of the subchannels 451, 452, and 453. When the sizes of the particles are sufficiently smaller than the widths of the subchannels 451, 452, and 453, the separation of the particles and the fluid can be more effectively performed than in the case where the sample movement unit 144 is formed as one channel, as illustrated in the centrifugal force-based microfluidic device 203 of FIG. 12.

Figure 14:
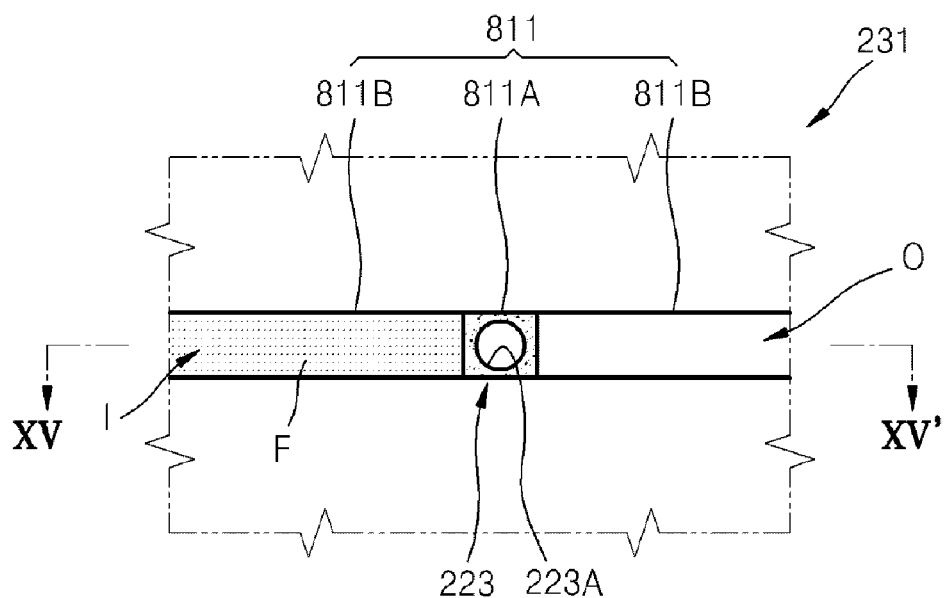
FIG. 14 is a plan view of a phase transition-type normally closed valve which can be used as a valve in the centrifugal force-based microfluidic devices of FIGS. 1, 3, 6A, 7, and FIGS. 10 through 13.
Figure 15:
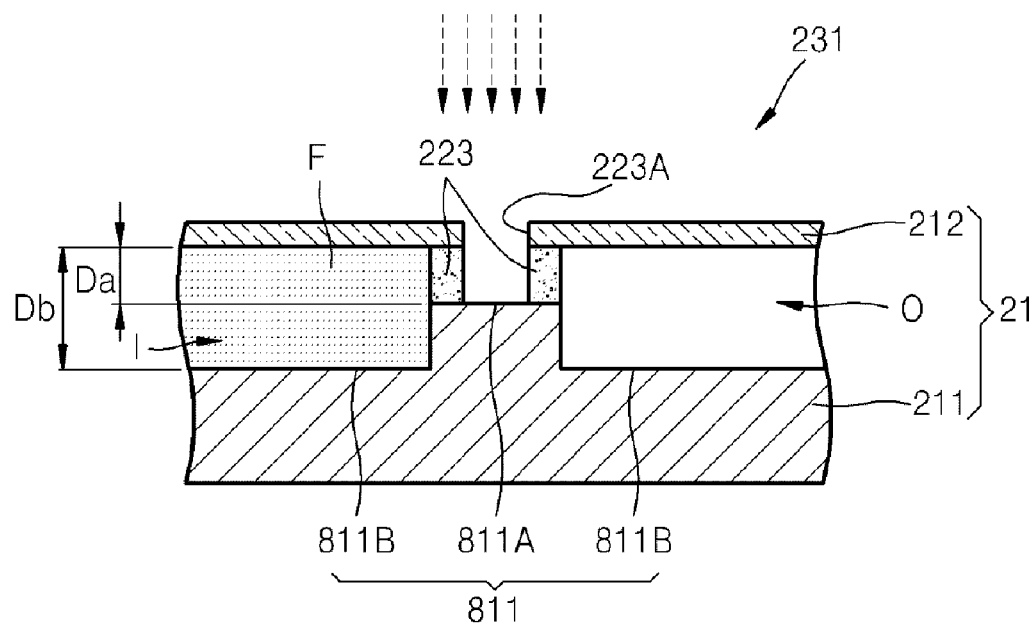
FIG. 15 is a cross-sectional view of the phase transition-type normally closed valve shown in FIG. 14 taken along line XV-XV'.

FIG. 14 is a plan view of a phase transition-type normally closed valve which can be used as valves of the centrifugal force-based microfluidic devices 100, 101, 103, 200, and 201 through 204 respectively of FIGS. 1, 3, 6A, 7, and FIGS. 10 through 13, and FIG. 15 is a cross-sectional view of the phase transition-type normally closed valve of FIG. 14 taken along line XV-XV'. The phase transition-type normally closed valve which can be used as the first outlet valve 231 and the first through fourth outlet valves 232, 233, and 234 will now be described.

The phase transition-type normally closed valve includes a valve plug 223 which is formed of a valve material in a solid state at room temperature. A material in which heat generating particles are dispersed in a phase transition material in a solid state at room temperature can be used as the valve material. The channel 811 comprises a first area 811A of a first dimension Da and a pair of second areas 811B adjacent to the first area 811A. The second areas 811B are of a second dimension Db larger than Da.

The valve plug 223 completely blocks without any gap a predetermined portion of the first area 811A which is not overlapped by an opening 223A and blocks the flow of fluid F flowing from an entrance "I". The valve plug 223 is melted at a high temperature and is moved from the first area 811A to the second areas 811B, and then the valve plug 223 is again solidified while flow paths of the fluid F are opened. The opening 223A functions as an injection hole which can define a valve plug 223 by injecting a valve material melted when manufacturing the microfluidic device. The valve material injected into the first area 811A through the opening 223A remains in the predetermined portion of the first area 811A by capillary action.

In order to heat the valve plug 223, external energy source 330L and 330P (see FIG. 20 and FIG. 21, respectively) is disposed outside the centrifugal force-based microfluidic device, and the external energy source 330L radiates an electromagnetic wave on the initial position of the valve plug 223, that is, on the opening 223A and a region including the circumference of the valve plug 223. The external energy source 330L may be a laser light source for radiating laser beams, and in that case, the external energy source 330L may include at least one laser diode. The laser light source may radiate a pulse laser having an energy of 1 mJ/pulse or higher, and may radiate a continuous wave laser having an output of 10 mW or higher.

A laser light source, for radiating a laser having a wavelength of 808 nm, was used in experiments by the inventors. However, the present invention is not limited to the radiation of laser beams having the wavelength of 808 nm, and a laser light source for radiating laser beams having a wavelength of 400-1300 nm can be used as the external energy source 330L of the microfluidic device.

The channel 811 is provided by cubic patterns that are formed inside the upper plate 212 or the lower plate 211 of the disc-shaped platform 21. The upper plate 212 is formed of an optically transparent material in which an electromagnetic wave radiated by the external energy source is transmitted incident on the valve plug 223, and thus, the flow of the fluid F can be observed from the outside due to the transparency. As an example thereof, glass or transparent plastic materials are advantageous in view of excellent optical transparency and low manufacturing cost.

The heat generating particles dispersed in the valve plug 223 have a diameter of 1 nm to 100 μm so as to freely flow within the channel 811 with a width of about several thousands of micrometers (μm). The heat generating particles have the characteristic in which, when a laser is radiated on the particles, the temperature of the heat generating particles rapidly rises due to the radiation energy of the laser, and the heat generating particles dissipate heat and are uniformly dispersed in a wax. Also, the heat generating particles may have a structure comprising a core including a metal component and a shell that has a hydrophobic property so as to have the above-described characteristic. For example, the heat generating particles may have a structure comprising a core formed of a ferromagnetic material, such as Fe, and a shell including a plurality of surfactants that are combined with Fe and which encompass Fe. Generally, the heat generating particles are kept in a state where the heat generating particles are dispersed in a carrier oil that may also have a hydrophobic property so that the heat generating particles that have a hydrophobic surface structure can be uniformly dispersed. The carrier oil in which the heat generating particles are dispersed is poured and mixed in the wax so that the material of the valve plug 223 can be manufactured. The shape of the heat generating particles is not limited to the shape as describe above and the heat generating particles can also be polymer beads, quantum dots, Au nanoparticles, Ag nanoparticles, beads with metal composition, carbon particles that include graphite particles or magnetic beads.

A phase transition material used in forming the valve plug 223 may be a wax.

When the energy of the electromagnetic wave that is absorbed by the heat generating particles is transmitted to the circumference in the form of a heat energy, the wax is melted and has fluidity and as such, the valve plug 223 collapses and the flow path of the fluid F is opened. The wax of the valve plug 223 may have a proper melting point. This is because, if a melting point is too high, the time during which the wax is melted after laser radiation starts is long and it is difficult to precisely control an opening time of the flow path of the fluid F and if a melting point is too low, the wax is partially melted when the laser is not radiated and the fluid F may leak. Also, the wax can be paraffin wax, microcrystalline wax, synthetic wax, natural wax, etc.

The phase transition material may also be gel or thermoplastic resin. The gel may be polyacrylamide, polyacrylates, polymethacrylates or polyvinylamides etc. In addition, the thermoplastic resin may be cyclic olefin copolymer (COC), polymethylmethacrylate (acrylic) (PMMA), polycarbonate (PC), polystyrene (PS), polyacetal engineering polymers (POM), perfluoroalkoxy (PFA), polyvinyl chloride (PVC), polypropylene (PP), polyethylene terephthalate (PET), polyetheretherketone (PEEK), polyamide (PA), polysulfone (PSU), polyvinylidene difluoride (PVDF), or the like.

Figure 16:
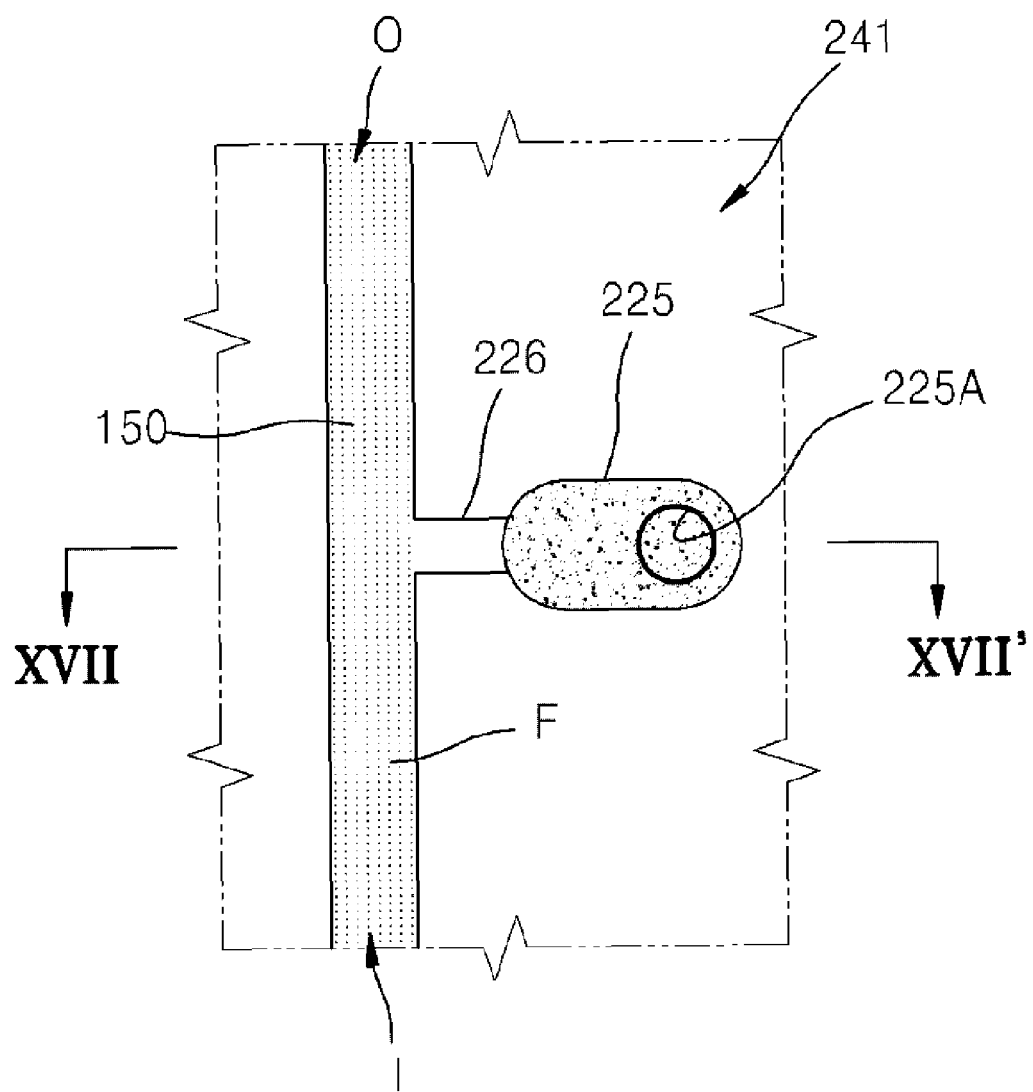
FIG. 16 is a plan view of a phase transition-type normally open valve that can be used in the centrifugal force-based microfluidic devices of FIGS. 10 through 13.
Figure 17:
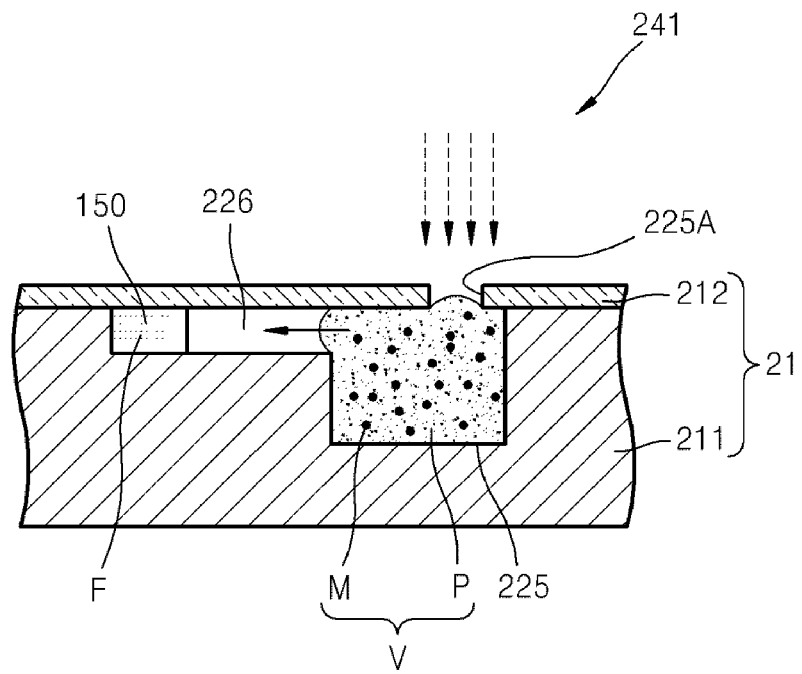
FIG. 17 illustrates the operation of the phase transition-type normally open valve shown in FIG. 16.

FIG. 16 is a plan view of a phase transition-type normally open valve which can be used in the centrifugal force-based microfluidic devices 201 through 204 respectively of FIGS. 10 through 13, according to an embodiment of the present invention, and FIG. 17 illustrates the operation of the phase transition-type normally open valve of FIG. 16.

As described above, in the embodiments of FIG. 10 through 13, a variety of valves may be used as the first and second normally open valves 241 and 242. In the present embodiment, an example of one of the first and second normally open valves 241 and 242 that can be used is the phase transition-type normally open valve. The phase transition-type normally open valve comprises a valve chamber 225 which is connected to a channel having an inlet I and an outlet O, that is, the fluid collecting channel 150 of FIG. 10 and to a part of the fluid collecting channel 150, and a valve material V which is inserted in the valve chamber 225 in a solid state at room temperature at an initial stage and, if the valve material V is heated, the valve material V is melted and expands, enters the fluid collecting channel 150, solidifies again and intercepts the flow of the fluid through the fluid collecting channel 150.

Like the above-described phase transition-type normally closed valve of FIG. 14, the phase transition-type normally open valve of the present embodiment may also be provided with cubic patterns that are formed inside the upper plate 212 or the lower plate 211 of the disc-shaped platform 21 of the centrifugal force-based microfluidic devices 201 through 204. The valve chamber 225 is formed to have a depth that is greater than the depth of the fluid collecting channel 150, for example, to have a depth of about 1 mm. The upper plate 212 is formed of an optically transparent material in which an electromagnetic wave radiated by an external energy source (not shown) is transmitted, and thus, a fluid sample L can be observed from the outside due to the transparency. Furthermore, the upper plate 212 may have an opening 225A corresponding to the valve chamber 225 so as to function as an injection hole through which the valve material V that melted when the centrifugal force-based microfluidic devices 201 through 204 are manufactured is injected.

The phase transition material P and the heat generating particles M of the valve material V are as described above using the example of the phase transition-type normally closed valve. In addition, the external energy sources 330P and 330L respectively of FIGS. 20 and 21, which provide an electromagnetic wave to the valve material V, is as described previously. If laser beams are radiated on the valve material V including the phase transition material P and the heat generating particles M, the heat generating particles M absorb the energy to heat the phase transition material P. As such, the valve material V is melted, expands, and enters the fluid collecting channel 150 through a connected path 226. The valve material V that is solidified again while contacting the fluid F within the fluid collecting channel 150 to form a valve plug so that the flow of the fluid sample F through the fluid collecting channel 150 is controlled.

The result of an experiment in which a reaction time of the above-described valve unit is measured is as follows. The pressure of a working fluid in a test chip for the experiment was kept at 46 kPa. A syringe pump (Havard PHD2000, USA) and a pressure sensor (MPX 5500DP, Freescale semiconductor Inc., AZ, USA) were used to keep the pressure constant at 46 kPa. A laser light source having an emission wavelength of 808 nm and an output of 1.5 W was used as an external energy source for radiating an electromagnetic wave to the valve unit. Data on the reaction time of the valve unit was obtained through a result analysis of a high-speed photographing device (Fastcam-1024, Photron, Calif., USA). A wax, which is called ferrofluid, in which magnetic beads having an average diameter of 10 nm as heat generating particles, are dispersed in a carrier oil, and a paraffin wax are mixed at the ratio of 1:1. That is, a so-called ferrowax, which has a volume fraction of a ferrofluid of 50%, may be used as the valve material.

A reaction time, which is the time from when the laser beams start to be radiated on the valve plug 223 of the phase transition-type normally closed valve shown in FIG. 14 until the valve plug 223 is melted and the channel 221L is opened, was 0.012 seconds. And, a reaction time, which is the time from when the laser beams start to be radiated on the valve material of the phase transition-type normally open valve shown in FIG. 16 until the valve material is melted and expands and the channel 221L is closed, was 0.444 seconds. Compared to the reaction time of a conventional wax valve of 2-10 seconds, one skilled in the art can understood that the reaction time is significantly faster.

Figure 18:
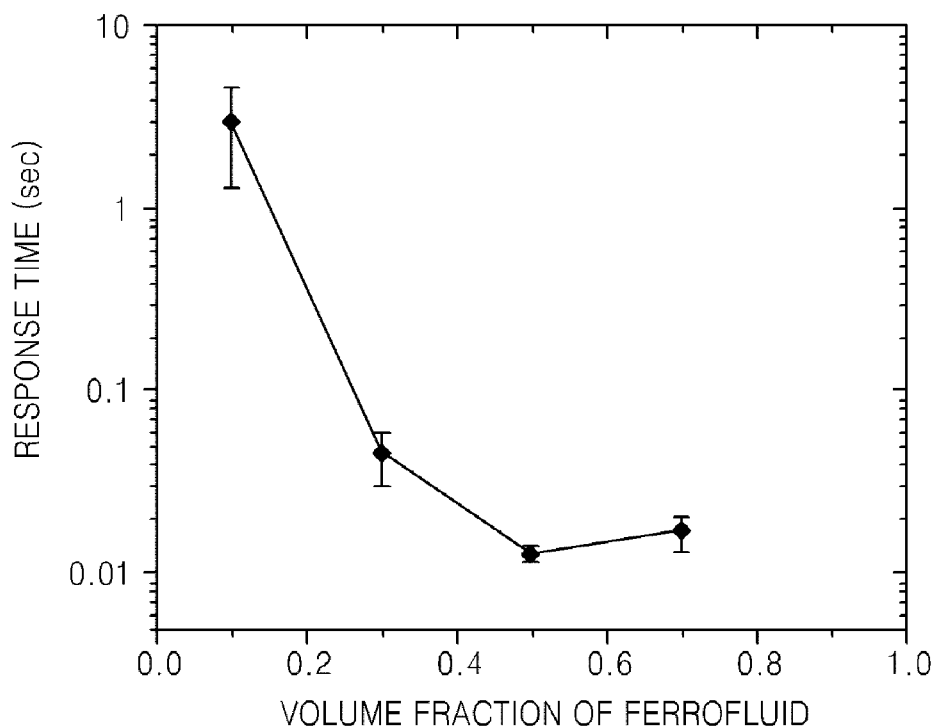
FIG. 18 is a graph showing the volume fraction of a ferrofluid (heat generating particle dispersion solution) according to a valve reaction time in a valve material used in the phase transition-type normally closed valve and the phase transition-type normally open valve, according to an exemplary embodiment of the present invention.

FIG. 18 is a graph showing the volume fraction of a ferrofluid (heat generating particle dispersion solution) according to a valve reaction time in a valve material used in the phase transition-type normally closed valve and the phase transition-type normally open valve. So-called magnetic beads are used as heat generating particles in the phase transition-type normally closed valve and the phase transition-type normally open valve, and the magnetic beads are provided in the form of a suspension that is generally dispersed in an oily medium, and which is commonly referred to as a ferrofluid. The above-described valve material is formed by mixing the phase transition material, such as a paraffin wax, with the ferrofluid. When the volume fraction of the ferrofluid increases, a reaction time is reduced. However, when the volume fraction of the ferrofluid increases to 70% or higher, the maximum hold-up pressure of the valve plug tends to be reduced. Thus, the volume fraction of the ferrofluid that is to be included in the valve plug in the valve unit is determined by compromising the demand for a fast reaction time and a demand for a high maximum hold-up pressure.

Figure 19:
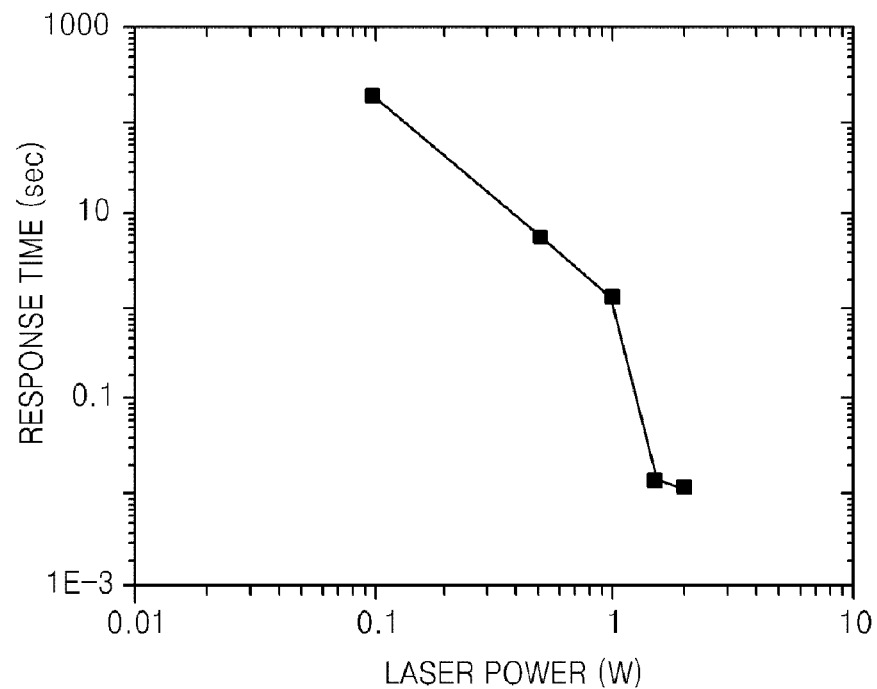
FIG. 19 is a graph showing power of a laser light source that is used as an external energy source when the phase transition-type normally closed valve and the phase transition-type normally open valve are driven, and a valve reaction time, according to an exemplary embodiment of the present invention.

FIG. 19 is a graph showing power of a laser light source that is used as an external energy source when the phase transition-type normally closed valve and the phase transition-type normally open valve are driven, and a valve reaction time, according to an embodiment of the present invention. As an output of the laser light source increases, a reaction time tends to be reduced. However, if the output of the laser light source is close to 1.5 W, a change in reaction time is subtle, and (although not shown in the graph), if the output of the laser light source exceeds 1.5 W, a predetermined minimum reaction time is converged upon because thermal conductivity is limited by paraffin wax. In the experiment, for this reason, a laser light source having an output of 1.5 W was used. However, the external energy source of the present invention is not limited to this.

Figure 20:
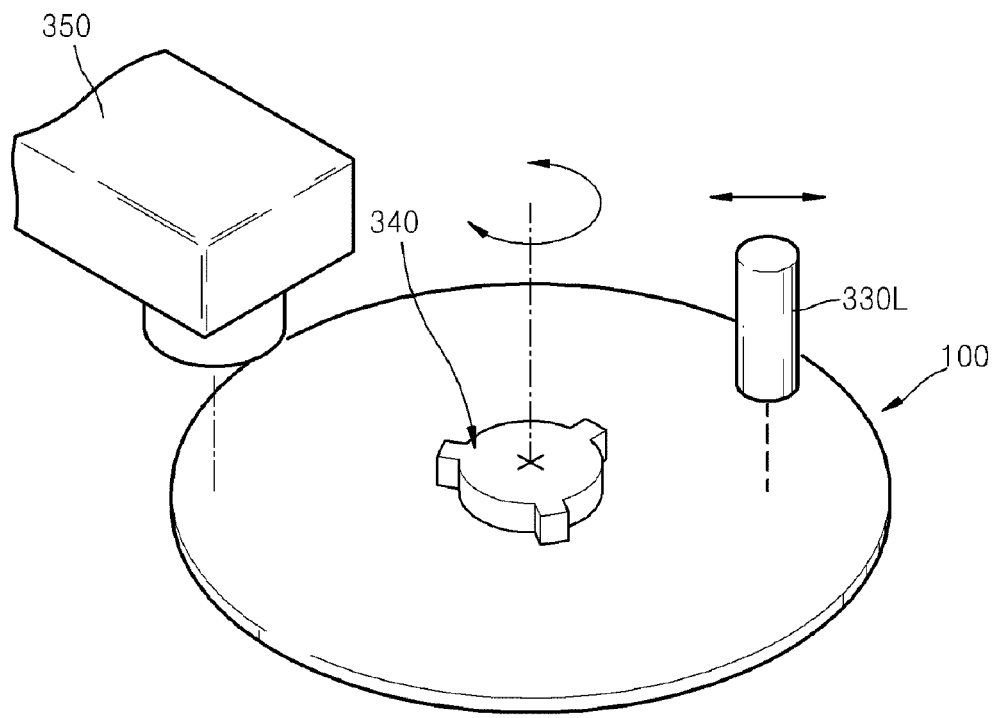
FIG. 20 is a perspective view of a centrifugal force-based microfluidic system according to an exemplary embodiment of the present invention.

FIG. 20 is a perspective view of a centrifugal force-based microfluidic system according to an embodiment of the present invention. The microfluidic system of FIG. 20 can comprise the above-described centrifugal force-based microfluidic devices 100~103 and 200~204. In the present embodiment, the centrifugal force-based microfluidic system comprising the centrifugal force-based microfluidic device 100 of FIG. 1 will now be described. The centrifugal force-based microfluidic system according to the present embodiment comprises an external energy source 330L which supplies an energy by radiating a predetermined electromagnetic wave on the first and second outlet valves 231 and 232 using the above-described separate driving method. The external energy source 330L is a device which radiates an electromagnetic wave having a predetermined wavelength selected from various electromagnetic waves having various wavelengths such as microwaves, infrared rays, visible rays, ultraviolet (UV) rays, and X-rays. In addition, a device which radiates a concentrated electromagnetic wave on a short-distance target is preferable. The wavelength of the external energy source 330L is in the range in which the energy is well absorbed by the heat generating particles included in the valve material. Thus, an element for generating an electromagnetic wave in the external energy source 330L is properly selected according to the material of the heat generating particles M and surface conditions. The external energy source 330L is a laser light source that radiates laser beams, and in that case, the external energy source 330L may comprise at least one laser diode. Details of the wavelengths and the outputs of the laser beams is determined according to the types of heat generating particles M included in the phase transition valve of the centrifugal force-based microfluidic device 100 that is mainly used.

The centrifugal force-based microfluidic system comprises an external energy source adjusting unit (not shown) which adjusts the position or direction of the external energy source 330L and allows a concentrated electromagnetic wave radiated by the external energy source 330L to reach a desired region of the centrifugal force-based microfluidic device 100, specifically, one of at least one of the first and second outlet valves 231 and 232 included in the centrifugal force-based microfluidic device 100. The external energy source adjusting unit (not shown) in a centrifugal force-based microfluidic system of FIG. 18 may move the external energy source 330L that is installed toward the disc-shaped platform 21 of the centrifugal force-based microfluidic device 100 in a direction of an arrow marked thereon, that is, in a radial direction of the disc-shaped platform 21. A mechanism for linearly moving the external energy source 330L is provided in various ways and is obvious to one skilled in the art and thus, a description thereof will be omitted.

The centrifugal force-based microfluidic system comprises a rotation driver 340 which drives the disc-shaped platform 21. Also, the rotation driver 340 is a part for seating the disc-shaped platform 21 and transmitting a rotative force, and although not shown, the rotation driver 340 may comprise a motor which rotates the disc-shaped platform 21 at a desired speed or at a desired angle and components related to the motor. Like the external energy source adjusting unit (not shown), an example of a specific construction of the rotation driver 340 will be omitted. In the centrifugal force-based microfluidic system of FIG. 18, the external energy source 330L may radiate an electromagnetic wave on a selected region of the centrifugal force-based microfluidic device 100 in a concentrated manner by means of the external energy source adjusting unit (not shown) and the rotation driver 340.

The centrifugal force-based microfluidic system according to the present invention may further comprise a photodetector 350 which can optically detect the result of centrifugal separation using the centrifugal force-based microfluidic device 100 and the results of various experiments using other functional units that can be included in the centrifugal force-based microfluidic device 100. For example, when the sample is separated and quantitatively-distributed serum is transported to the first test unit 81 (see FIG. 7), the photodetector 350 may optically detect a reaction of the serum and a reagent that has already been injected in the first test unit 81 (for example, a reagent that indicates whether a particular antibody or antigen exists in the serum through fluorescent revelation).

Figure 21:
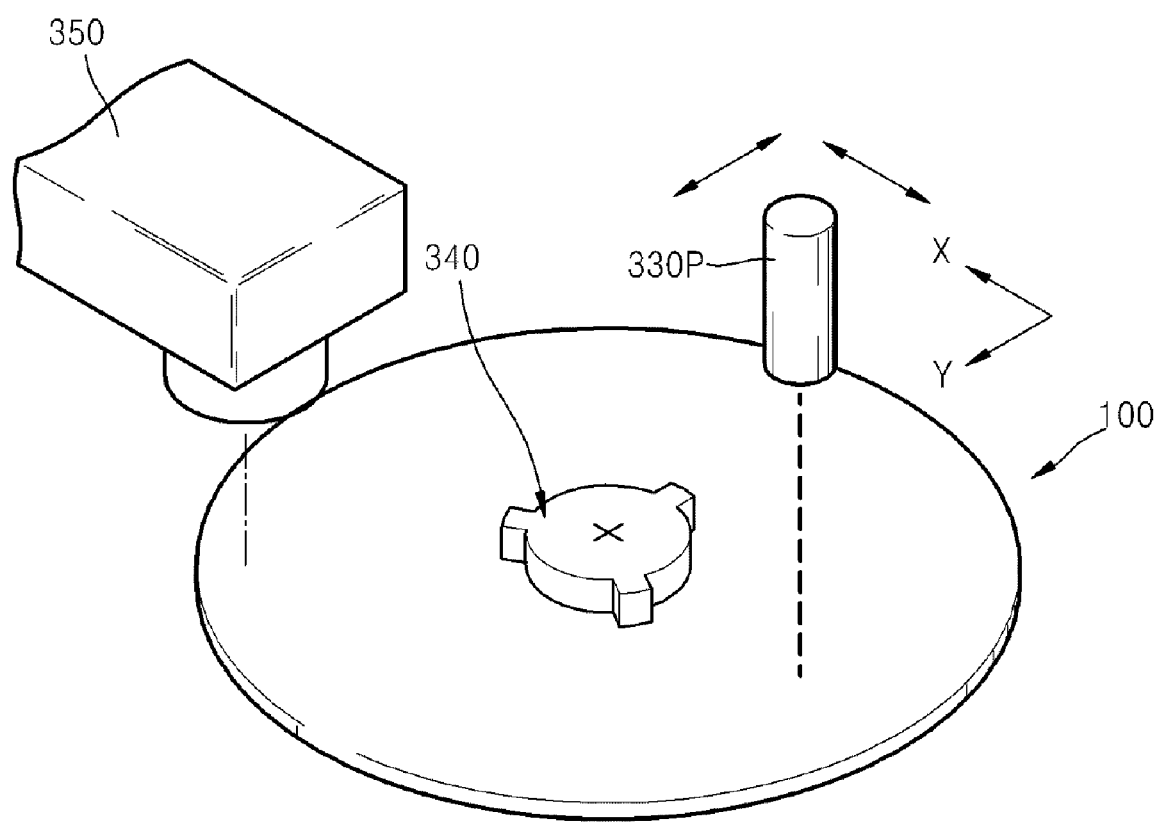
FIG. 21 is a perspective view of a centrifugal force-based microfluidic system according to another exemplary embodiment of the present invention.

FIG. 21 is a perspective view of a centrifugal force-based microfluidic system according to another embodiment of the present invention. In the centrifugal force-based microfluidic system according to the present embodiment, the centrifugal force-based microfluidic device 100, the rotation driver 340, and the external energy source 330P are described as the embodiment of FIG. 20. However, the centrifugal force-based microfluidic system according to the present embodiment may comprise a plane moving unit which moves the external energy source adjusting unit (not shown) that moves the external energy source 330P installed toward the disc-shaped platform 21 in two directions in which the external energy source adjusting unit crosses the disc-shaped platform 21 at right angles on a plane parallel to the disc-shaped platform 21, for example, x-axis and y-axis directions of the drawing (see arrows), so that an electromagnetic wave reaches a target spot on the disc-shaped platform 21.

In addition, although not shown, the external energy adjusting unit is formed to change the direction of the external energy source of which position is fixed in one place of an upper portion of the disc-shaped platform 21 to allow the emitted electromagnetic wave to reach a target spot.

The centrifugal force-based microfluidic device and the microfluidic system including the same according to the present invention can separate a fluid and particles from a sample, including the fluid and the particles, within a disc-shaped platform using a centrifugal force and can distribute the separated fluid quantitatively without the need for performing an additional metering operation.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A centrifugal force-based microfluidic device comprising:
    a disc-shaped platform, which can be rotated;
    a sample injection hole, which is disposed at one side of the disc-shaped platform;
    a sample separation unit of which one end is connected to the sample injection hole, and which is extended toward the outside of the disc-shaped platform so as to provide a space in which a sample, including particles injected through the sample injection hole, is centrifugally separated into the particles and a fluid by rotation of the disc-shaped platform;
    a fluid collecting unit, which is connected to a radially inner end of the sample separation unit, and which accommodates a surplus fluid that exceeds a predetermined capacity of the sample separation unit; and
    at least one outlet valve, which is connected to the sample separation unit, is separately driven, and is disposed in a position in which a fluid having a certain volume of the separated fluid within the sample separation unit can be discharged by rotation of the disc-shaped platform, without use of a separate metering chamber.

2. The device of claim 1, further comprising a particle collecting unit, which is disposed at a radially outer end of the sample separation unit, is connected to the sample separation unit, and provides a space in which particles separated by centrifugal separation are collected.

3. The device of claim 2, wherein the particle collecting unit is formed to have a depth that is greater than a depth of the sample separation unit, so that a step portion is formed at an interface between the particle collecting unit and the sample separation unit.

4. The device of claim 1, wherein the depth of the sample separation unit gradually increases radially toward the outside of the disc-shaped platform.

5. The device of claim 1, further comprising a sample storing unit, which is disposed at a radially inner end of the sample separation unit, is connected to the sample injection hole and accommodates the sample injected through the sample injection hole.

6. The device of claim 1, wherein the fluid collecting unit comprises a channel that is connected to the sample separation unit and a valve that controls a flow of the fluid through the channel passively or actively.

7. The device of claim 1, further comprising a particle collecting unit, which is disposed at a radially outer end of the sample separation unit, is connected to the sample separation unit, and provides a space in which particles separated by centrifugal separation are collected.

8. The device of claim 7, wherein the particle collecting unit is formed to have a depth that is greater than a depth of the sample separation unit so that a step portion is formed at an interface between the particle collecting unit and the sample separation unit.

9. The device of claim 7, wherein the depth of the sample separation unit gradually increases radially toward the outside of the disc-shaped platform.

10. The device of claim 1, wherein the sample separation unit is disposed to have an inclination with respect to a radial direction of the disc-shaped platform.

11. A centrifugal force-based microfluidic system comprising:
a centrifugal force-based microfluidic system comprising a disc-shaped platform which can be rotated;
a sample injection hole which is disposed at one side of the disc-shaped platform;
a sample separation unit of which one end is connected to the sample injection hole, which is extended toward the outside of the disc-shaped platform, and which provides a space in which a sample, including particles injected through the sample injection hole, is centrifugally separated into the particles and a fluid by rotation of the disc-shaped platform;
a fluid collecting unit, which is connected to a radially inner end of the sample separation unit, and which accommodates a surplus fluid that exceeds a predetermined capacity of the sample separation unit; and
at least one outlet valve, which is connected to the sample separation unit, is separately driven and is disposed in a position in which a fluid having a certain volume of the separated fluid within the sample separation unit can be discharged by rotation of the disc-shaped platform, without use of a separate metering chamber;
a rotation driver, which supports the centrifugal force-based microfluidic device and controllably rotates the centrifugal force-based microfluidic device; and
a valve driving unit, which separately drives a valve, of the at least one outlet valve, selected in the centrifugal force-based microfluidic device.

12. The system of claim 11, wherein the valve driving unit comprises:
an external energy source, which emits an electromagnetic wave capable of inducing heating of the heat generating particles within the valve; and an external energy source adjusting unit, which adjusts the position or direction of the external energy source so that an electromagnetic wave radiated by the external energy source can reach a region, which corresponds to the selected valve.

13. The system of claim 12, wherein the external energy source adjusting unit comprises a linear movement unit, which moves the external energy source that is installed toward the disc-shaped platform of the centrifugal force-based microfluidic device in a radial direction of the disc-shaped platform.

14. The device of claim 13, wherein the sample movement unit is divided into at least one barrier rib, which is disposed in a longitudinal direction and provides a plurality of flow paths.

15. The system of claim 12, wherein the external energy source adjusting unit comprises a plane moving unit, which moves the external energy source installed toward the disc-shaped platform in two directions on a plane parallel to the disc-shaped platform according to rectangular coordinates.

16. A centrifugal force-based microfluidic device comprising:
a platform which can be rotated;
a sample injection hole, which is disposed at one side of the platform;
a sample movement unit of which one end is connected to the sample injection hole and which is extended toward the outside of the platform;
a particle collecting unit, which is disposed at an outer end of the sample movement unit so as to provide a space in which particles having relatively high densities can be collected from the sample movement unit by rotation of the platform;
a fluid collecting channel, which is connected to the particle collecting unit and of which an inner end is connected to a vent hole disposed to be nearer to a rotation center of the platform than the particle collecting unit so that a fluid of a sample is collected by rotation of the platform; and
at least one outlet valve, which is connected to the fluid collecting channel, is separately driven and is disposed in a position in which a fluid having a certain volume of the separated fluid within the fluid collecting channel can be discharged by rotation of the platform.

17. The device of claim 16, wherein an outer end of the fluid collecting channel is connected to the particle collecting unit and a depth of the fluid collecting channel is less than that of the particle collecting unit so that a step portion is formed at an interface between the particle collecting unit and the fluid collecting channel.

18. The device of claim 16, wherein the particle collecting unit is formed to have a depth that is greater than the sample movement unit so that a step portion is formed between the particle collecting unit and the sample movement unit.

19. The device of claim 18, wherein a depth of the fluid collecting channel is less than that of the sample movement unit.

20. The device of claim 16, wherein the depth of the sample separation unit gradually radially increases toward the outside of the platform.

21. The device of claim 16, further comprising a sample storing unit, which is disposed at a radially inner end of the sample movement unit, is connected to the sample injection hole and accommodates the sample injected through the sample injection hole.

22. The device of claim 16, wherein the centrifugal force-based microfluidic device further comprises a normally open valve, which is disposed between the particle collecting unit and the outlet valve nearest the particle collecting unit and closes the fluid collecting channel.

23. The device of claim 16, wherein the sample movement unit is disposed so that the sample movement unit has a declining bottom surface in a radial direction of the platform.

24. A centrifugal force-based microfluidic system comprising:

a platform, which can be rotated;
a sample injection hole, which is disposed at one side of the platform;
a sample movement unit of which one end is connected to the sample injection hole and which is extended toward an outside of the platform;
a particle collecting unit, which is disposed at an outer end of the sample movement unit so as to provide a space in which particles having relatively high densities can be collected from the sample movement unit by rotation of the platform;
a fluid collecting channel, which is connected to the particle collecting unit and of which an inner end is connected to a vent hole disposed to be nearer to a rotation center of the platform than the particle collecting unit so that a fluid of a sample is collected by rotation of the platform; and
at least one outlet valve, which is connected to the fluid collecting channel, is separately driven and is disposed in a position in which a fluid having a certain volume of the separated fluid within the fluid collecting channel can be discharged by rotation of the platform;
a rotation driver, which supports the centrifugal force-based microfluidic device and controllably rotates the centrifugal force-based microfluidic device; and
a valve driving unit, which separately drives a valve, of the at least one outlet valve, selected in the centrifugal force-based microfluidic device.

25. A centrifugal force-based microfluidic device comprising:
a platform which is operative to be rotated;
a sample injection hole, disposed at one side of the platform;
a sample separation unit of which one end is connected to the sample injection hole, and which extends toward the outside of the platform to provide a space in which a sample is centrifugally separated;
a fluid collecting unit, which is connected to a radially inner end of the sample separation unit, and which accommodates a surplus fluid that exceeds a predetermined capacity of the sample separation unit; and
at least one outlet valve connected to the sample separation unit, is separately driven, and is disposed in a position which is operative to discharge a predetermined amount of fluid from the sample separation unit by rotation of the platform, without use of a separate metering chamber.

* * * * *